(12) United States Patent
Fischer et al.

(10) Patent No.: US 11,407,720 B2
(45) Date of Patent: Aug. 9, 2022

(54) COMPOUNDS HAVING A STABILIZING EFFECT, METHOD FOR PRODUCING SAID COMPOUNDS, COMPOSITION CONTAINING SAID STABILIZING COMPOUNDS, AND USES OF THE COMPOUNDS

(71) Applicant: FRAUNHOFER-GESELLSCHAFT ZUR FÖRDERUNG DER ANGEWANDTEN FORSCHUNG E. V., Munich (DE)

(72) Inventors: Johannes Fischer, Schlangenbad (DE); Elke Metzsch-Zillingen, Steffeln (DE); Rudolf Pfaendner, Rimbach (DE)

(73) Assignee: Fraunhofer-Gesellschaft zur förderung der angewandten Forschung e.V., Munich (DE)

( * ) Notice: Subject to any disclaimer, the term of this patent is extended or adjusted under 35 U.S.C. 154(b) by 0 days.

(21) Appl. No.: 16/764,291

(22) PCT Filed: Nov. 14, 2018

(86) PCT No.: PCT/EP2018/081270
§ 371 (c)(1),
(2) Date: May 14, 2020

(87) PCT Pub. No.: WO2019/096868
PCT Pub. Date: May 23, 2019

(65) Prior Publication Data
US 2020/0361879 A1 Nov. 19, 2020

(30) Foreign Application Priority Data

Nov. 17, 2017 (DE) ...................... 10 2017 220 555.5

(51) Int. Cl.
| | | |
|---|---|---|
| *C07D 251/32* | (2006.01) | |
| *C07C 323/12* | (2006.01) | |
| *C07C 323/13* | (2006.01) | |
| *C07C 323/16* | (2006.01) | |
| *C07D 251/34* | (2006.01) | |
| *C08K 5/372* | (2006.01) | |
| *C08K 5/375* | (2006.01) | |
| *C09K 15/14* | (2006.01) | |

(52) U.S. Cl.
CPC .......... *C07D 251/32* (2013.01); *C07C 323/12* (2013.01); *C07C 323/13* (2013.01); *C07C 323/16* (2013.01); *C07D 251/34* (2013.01); *C08K 5/375* (2013.01); *C08K 5/3725* (2013.01); *C09K 15/14* (2013.01)

(58) Field of Classification Search
CPC .. C07D 251/32; C07D 251/34; C07C 323/12; C07C 323/13; C07C 323/16; C08K 5/3725; C08K 5/375; C09K 15/14
See application file for complete search history.

(56) References Cited

U.S. PATENT DOCUMENTS

| | | | |
|---|---|---|---|
| 2,617,778 A | | 11/1952 | Gluesenkamp |
| 2,642,373 A | | 6/1953 | Dazzi |
| 2,981,717 A | | 4/1961 | Boultbee |
| 3,245,992 A | | 4/1966 | Dexter et al. |
| 3,257,354 A | | 6/1966 | Dexter et al. |
| 3,285,855 A | | 11/1966 | Dexter et al. |
| 3,763,094 A | * | 10/1973 | Knell .................. C08K 5/378 524/100 |
| 3,763,221 A | * | 10/1973 | Hechenbleikner .... C07C 323/00 560/75 |
| 3,821,334 A | * | 6/1974 | Brunetti ................ C07C 49/245 558/87 |
| 3,856,846 A | * | 12/1974 | Eggensperger ....... C07C 323/00 558/378 |
| 3,914,319 A | * | 10/1975 | Dear ..................... C08K 5/375 568/46 |
| 3,927,150 A | * | 12/1975 | Schwarzenbach ..... C08K 5/527 558/74 |
| 3,954,839 A | * | 5/1976 | Dexter ................ C08K 5/1345 560/75 |
| 3,988,363 A | * | 10/1976 | Spivack .................. C07C 59/52 560/75 |

(Continued)

FOREIGN PATENT DOCUMENTS

| | | |
|---|---|---|
| CA | 1005456 A | 2/1977 |
| CA | 2029708 C | 7/2003 |

(Continued)

OTHER PUBLICATIONS

CAS Abstract and Indexed Compound, M. Knell et al., U.S. Pat. No. 3,763,094 (1973) (Year: 1973).*
CAS Abstract of M. Dexter et al., GB 996502 (1964) (Year: 1964).*
L. Campos et al., PMSE Preprints (2010) (Year: 2010).*
Hawley's Condensed Chemical Dictionary, p. 1275 (16th ed., 2016, R.J. Larrañaga ed.) (Year: 2016).*
M. Montañez et al., 43 Macromolecules, 6004-6013 (2010) (Year: 2010).*
J. Fischer et al., 173 Polymer Degradation and Stability (2020) (Year: 2020).*
J. Bruhn et al., 61 Helvetica Chimica Acta, 2542-2559 (1978) (Year: 1978).*
V. Bilinski et al., 66 Helvetica Chimica Acta, 2322-2329 (1983) (Year: 1983).*

(Continued)

*Primary Examiner* — Alexander R Pagano
(74) *Attorney, Agent, or Firm* — Leydig, Voit & Mayer, Ltd.

(57) ABSTRACT

The invention relates to compounds of a new type which have a stabilizing effect and in particular provide stabilization with respect to oxidative thermal and/or actinic decomposition of or damage to organic materials. The compounds are represented by general formula I specified below. The invention further relates to a method for producing such compounds, to compositions containing said compound, to a method for stabilizing organic compounds by means of the stabilizing compounds, and to the use of the stabilizing compounds to stabilize organic materials.

13 Claims, No Drawings

(56) References Cited

U.S. PATENT DOCUMENTS

| | | | |
|---|---|---|---|
| 4,035,337 A | 7/1977 | Herweh et al. | |
| 4,633,008 A | 12/1986 | Oonishi et al. | |
| 4,694,102 A | 9/1987 | Oonishi et al. | |
| 4,727,103 A | 2/1988 | Dunski | |
| 4,874,885 A | 10/1989 | Stegmann et al. | |
| 5,041,616 A * | 8/1991 | Sumner, Jr. | C07C 67/08 |
| | | | 560/144 |
| 6,174,940 B1 * | 1/2001 | Stahrfeldt | C08K 5/353 |
| | | | 524/99 |
| 8,871,869 B2 * | 10/2014 | Dias | C08J 7/056 |
| | | | 525/218 |
| 10,138,354 B2 | 11/2018 | Groos et al. | |
| 10,214,631 B2 | 2/2019 | Pfaendner et al. | |
| 10,323,136 B2 | 6/2019 | Pfaendner et al. | |
| 10,364,340 B2 | 7/2019 | Pfaendner et al. | |
| 10,370,537 B2 | 8/2019 | Pfaendner et al. | |
| 10,450,442 B2 | 10/2019 | Pfaendner et al. | |
| 10,544,284 B2 | 1/2020 | Pfaendner et al. | |
| 10,781,296 B2 | 9/2020 | Groos et al. | |
| 2013/0317168 A1 * | 11/2013 | Buhler | C08L 77/06 |
| | | | 524/607 |
| 2016/0052927 A1 | 2/2016 | Pfaendner et al. | |
| 2016/0272789 A1 | 9/2016 | Pfaendner et al. | |
| 2017/0107375 A1 | 4/2017 | Pfaendner et al. | |
| 2017/0121499 A1 | 5/2017 | Pfaendner et al. | |
| 2017/0260362 A1 | 9/2017 | Pfaendner et al. | |
| 2017/0260363 A1 | 9/2017 | Pfaendner et al. | |
| 2017/0260366 A1 | 9/2017 | Pfaendner et al. | |
| 2017/0267835 A1 | 9/2017 | Groos et al. | |
| 2018/0186970 A1 | 7/2018 | Groos et al. | |
| 2019/0248927 A1 | 8/2019 | Klein et al. | |
| 2020/0231783 A1 | 7/2020 | Pfaendner et al. | |
| 2020/0239805 A1 * | 7/2020 | Zhang | C10M 135/26 |
| 2020/0317886 A1 | 10/2020 | Pfaendner et al. | |
| 2020/0361879 A1 | 11/2020 | Fischer et al. | |

FOREIGN PATENT DOCUMENTS

| | | | | |
|---|---|---|---|---|
| DE | 2 364 126 A1 | 7/1974 | | |
| DE | 251128 A1 | 11/1987 | | |
| DE | 3 639 400 A1 | 5/1988 | | |
| EP | 0 275 832 A1 | 7/1988 | | |
| EP | 0 428 973 A1 | 5/1991 | | |
| GB | 996502 A * | 6/1965 | ........... | C08K 5/1345 |
| GB | 1103145 A | 2/1968 | | |
| GB | 1451118 A * | 9/1976 | ............ | C09K 15/14 |
| GB | 1451118 A | 9/1976 | | |
| WO | WO 86/00301 A1 | 1/1986 | | |
| WO | WO 2004/033699 A1 | 4/2004 | | |

OTHER PUBLICATIONS

Hoyle et al., "Thiol-ene click chemistry," *Angew Chem Int Ed Engl* 49(9): 1540-1573 (2010).

Kröhnke et al., "Antioxidants," *Uhlmann's Encyclopedia of Industrial Chemistry*, Wiley-VCH Verlag GmbH & Co. KGaA, pp. 1-36 (2015).

Li et al., "Preparation, Structural Characterization, and Antioxidative Behavior in Natural Rubber of Antioxidant GM Functionalized Nanosilica," *Polymer Composites*, pp. 1-7 (2015).

Limnios et al., "Photoinitiated Thiol-Ene "Click" Reaction: An Organocatalytic Alternative," *Adv. Synth. Catalysis* 359(2): 323-328 (2017).

Otera, "Transesterification," *Chem. Rev.* 93(4): 1449-1470 (1993).

Wu et al., "Synthesis and Characterization of A Novel Macromolecular Hindered Phenol Antioxidant and Its Thermo-Oxidative Aging Resistance for Natural Rubber," *J. Macromol. Sci. B: Phys* 53(7): 1244-1257 (2014).

Altintaş et al., "Thioether functional chain extender for thermoplastic polyurethanes," *Chinese Journal of Polymer Science* 33(6): 850-856 (2015).

Lowe, "Thiol-ene "click" reactions and recent applications in polymer and materials synthesis," *Polym Chem* 1: 17-36 (2010).

Vulic et al., "Structure-property relationships: phenolic antioxidants with high efficiency and low colour contribution," *Polym. Degrad. Stab* 78(1): 27-34 (2002).

European Patent Office, International Search Report in International Application No. PCT/EP2018/081270 (dated Feb. 21, 2019).

European Patent Office, Written Opinion in International Application No. PCT/EP2018/081270 (dated Feb. 21, 2019).

International Bureau of WIPO, International Preliminary Report on Patentability in International Application No. PCT/EP2018/081270 (dated May 19, 2020).

China National Intellectual Property Administration, Office Action in Chinese Patent Application No. 2018800851185 (dated Oct. 29, 2021).

Taiwan Intellectual Property Office, Examination Report in Taiwanese Patent Application No. 107140839 (dated May 9, 2022).

\* cited by examiner

COMPOUNDS HAVING A STABILIZING EFFECT, METHOD FOR PRODUCING SAID COMPOUNDS, COMPOSITION CONTAINING SAID STABILIZING COMPOUNDS, AND USES OF THE COMPOUNDS

CROSS-REFERENCE TO RELATED APPLICATIONS

This patent application is the U.S. national phase of International Application No. PCT/EP2018/081270, filed on Nov. 14, 2018, which claims the benefit of German Patent Application No. 10 2017 220 555.5, filed Nov. 17, 2017, the disclosures of which are incorporated herein by reference in their entireties for all purposes.

The present invention relates to novel compounds having a stabilizing effect, in particular a stabilization with respect to an oxidative thermal and/or actinic degradation of or damage to organic materials. The compounds are represented by the general formula I shown below. The present invention additionally relates to a method of manufacturing such compounds, to compositions containing said compound, to a method of stabilizing organic components with the aid of stabilizing compounds, and to a use of said stabilizing compounds for the stabilization of organic materials.

Organic materials such as plastics are subject to aging processes that ultimately result in a loss of the desired properties such as of the mechanical characteristic values. This process, called autoxidation, results, starting from radical chain scissions, in changes to the polymer chain such as in the molecular weight or in the formation of new chemical groups due to mechanochemical processes or due to UV radiation in the presence of oxygen. Stabilizers are therefore used to prevent or at least to delay this aging. Important representatives of stabilizers include antioxidants that interfere with the radicals formed in the autoxidation and thus interrupt the degradation process. A distinction is generally made between primary antioxidants that can react directly with free radicals containing oxygen or with C radicals and secondary antioxidants that react with intermediately formed hydroperoxides (see C. Kröhnke et al. Antioxidants in Ullmann's Encyclopedia of Industrial Chemistry, Wiley-VCH Verlag, Weinheim 2015). Typical representatives of primary antioxidants include, for example, phenolic antioxidants, amines, but also lactones. Classes of secondary antioxidants include phosphorus compounds such as phosphites and phosphonites, but also thio compounds such as sulfides and disulfides. The mutual use of primary and secondary antioxidants can here result in a synergetic effect. The combinations of phenolic antioxidants with phosphites/phosphonites, but also the combination of phenolic antioxidants with thio compounds (see e.g. I. Vulic et al. Pol. Degr. Stab. 2002, 78, 27-34).

Against the background of a synergetic effect, it is therefore also desirable to develop stabilizers that have both functions, namely that of the primary and secondary antioxidant effects, in one molecule.

Antioxidants containing sulfur, i.e. stabilizers, that contain both a sterically hindered phenolic group and a thio group in one molecule, are generally known and are also commercially available in part. Commercial products here have the following structures, for example (trade names, e.g.: Songnox 4150, Irganox 1081, Irganox 1035, Irganox 1520, Irganox 565, Hostanox OSP 1):

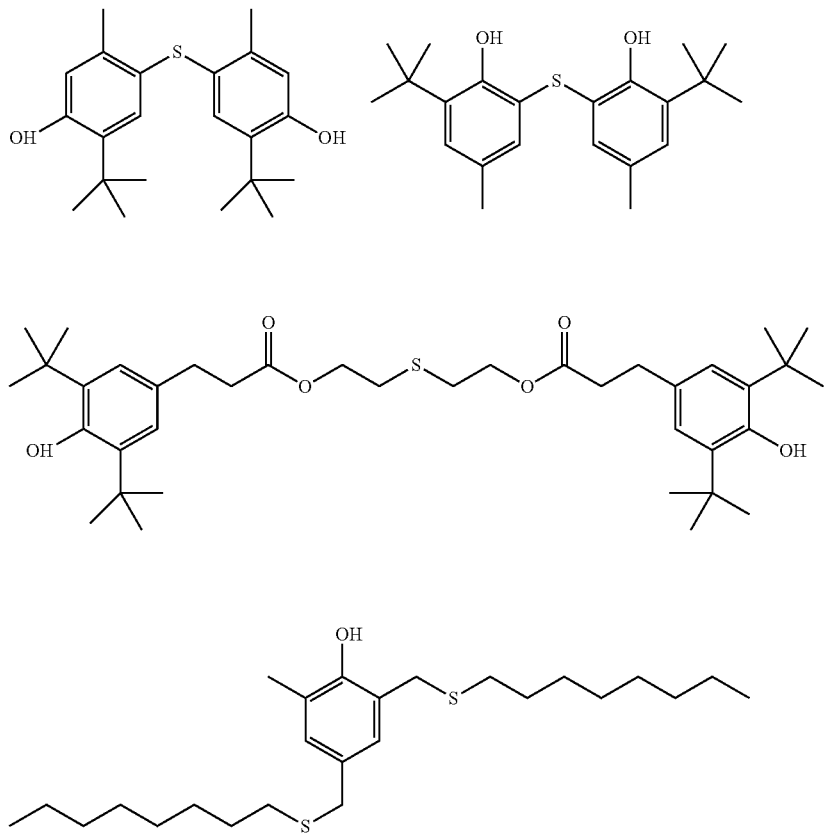

-continued

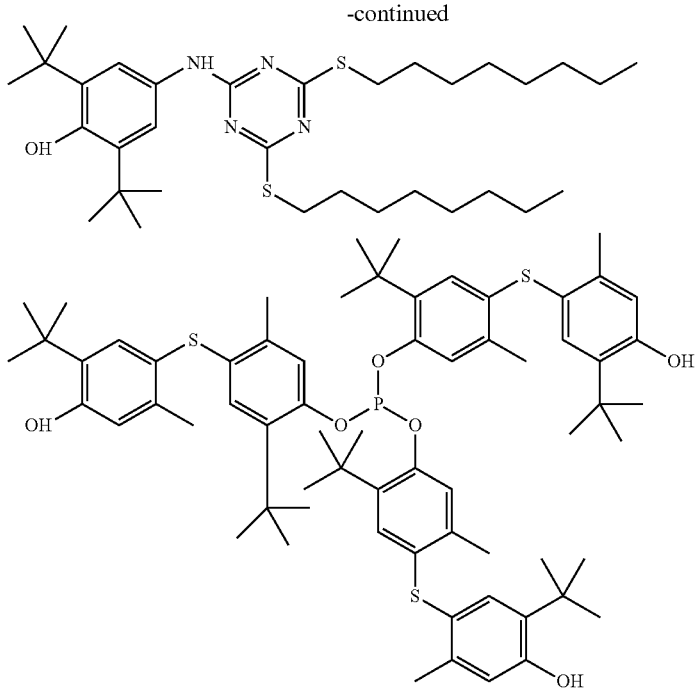

The synthesis and use of these stabilizers has been described in a large number of patents; there are mentioned by way of example: DE 23641126, DD 251128, EP 275832, EP 428973, U.S. Pat. Nos. 3,245,992, and 3,257,354.

It is furthermore known that aliphatic thio groups have a smaller discoloration tendency than aromatic thio groups (e.g. U.S. Pat. No. 2,981,717), which is generally a desired property for a long-term stability of organic materials.

Further stabilizers that include both phenolic and thio groups are described in the form of molecules containing isocyanurate in the patent specifications U.S. Pat. Nos. 4,727,103, 4,633,008 and 4,694,102. The chemical structures mentioned in these patents are prepared differently both from the structures in accordance with the invention and in accordance with other processes.

It is striking on an observation of the above-named commercial antioxidants containing sulfur that there are evidently no commercial products that simultaneously have a high concentration of sterically hindered phenols and a high concentration of aliphatic thio groups.

It was therefore the object of the present invention to provide a new method of preparing antioxidants containing sulfur and new compounds having an excellent stabilizing effectiveness for organic materials, in particular for plastics.

This object is achieved by the novel compounds in accordance with the general formula I and the preparation of the corresponding compounds. The subject matter of the present invention is additionally a composition containing an organic component to be stabilized and one of the compounds in accordance with the invention. The invention additionally relates to a method of stabilizing a stabilizing organic component and to uses of the stabilizing compounds in accordance with the invention. The respective advantageous embodiments are also described.

The invention thus relates to a compound in accordance with the general formula I

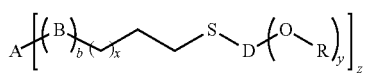

Formula I where the variables A, B, D, R, b, x, y, z each have the following definition independently of one another:
A an aromatic, unsaturated or saturated residue;
B O or NH;
D a linear or branched aliphatic residue having 1 to 12 carbon atoms;
R a residue having at least one sterically hindered group and at least one hydroxyl group;
b 0 or 1;
x 0 to 12;
y 1 to 4; and
z 1 to 6.

New stabilizers and a new method of preparing the stabilizers are proposed that permit a simple accessibility for complex stabilizer structures and have a high effectiveness e.g. in polymers. The high proportion of aliphatic sulfur groups due to the method in accordance with the invention with a simultaneously high number of sterically hindered phenol groups in particular results in a low discoloration tendency of the new compounds with a simultaneously extraordinary long-term stabilization.

It has surprisingly been found that the preceding compounds have a high stabilizing potential, in particular a stabilization of organic materials with respect to thermal and/or actinic degradation.

A preferred embodiment provides that the variable A is selected from the group comprising respective z-valent cyanuric acid residues, where z is 1 to 6 ; triazine residues; cyclic aliphatic hydrocarbon residues having 5 to 36 carbon atoms, in particular cyclohexyl; aromatic hydrocarbon residues, in particular phenyl; and linear or branched aliphatic hydrocarbon residues having 2 to 36 carbon atoms.

It is furthermore advantageous if the variable R here represents a grouping having at least one sterically hindered hydroxyphenyl residue and in particular has the following meaning

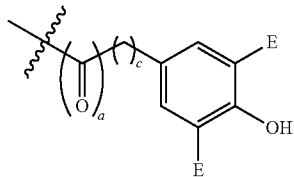

where
- E is the same or is different on every occurrence and represents a linearly aliphatic, branched aliphatic, or cycloaliphatic alkyl residue having 1 to 18 carbon atoms, an aromatic residue having 6 to 36 carbon atom or hydrogens, in particular a tert-butyl group or a methyl group;
- a is 1 or 0; and
- c is 0, 1, 2, 3, or 4.

Both residues E are preferably the same residues. It is, however, equally possible that the residues E are different; for example one residue E can be hydrogen and the other residue E can represent a methyl group or a t-butyl group.

The variables x, y, and z in particular have the following meaning independently of one another:
- x 0 or 1;
- y 1 or 2; and
- z 1, 2, 3 or 4.

The compound in accordance with the invention of the general formula I is preferably selected from the group comprising the following compounds:

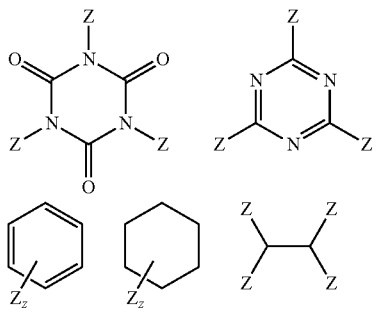

where Z has the following meaning;

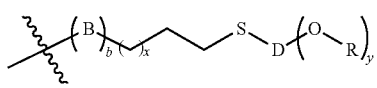

and the variables B, D, R, b, x, y, and z are defined herein.

The variable D is in particular selected from the group comprising —CH$_2$— or a 1, 2, 3-propinyl residue.

Particularly preferred embodiments of the present invention provide that the compound in accordance with the invention is selected from the group of the following compounds:

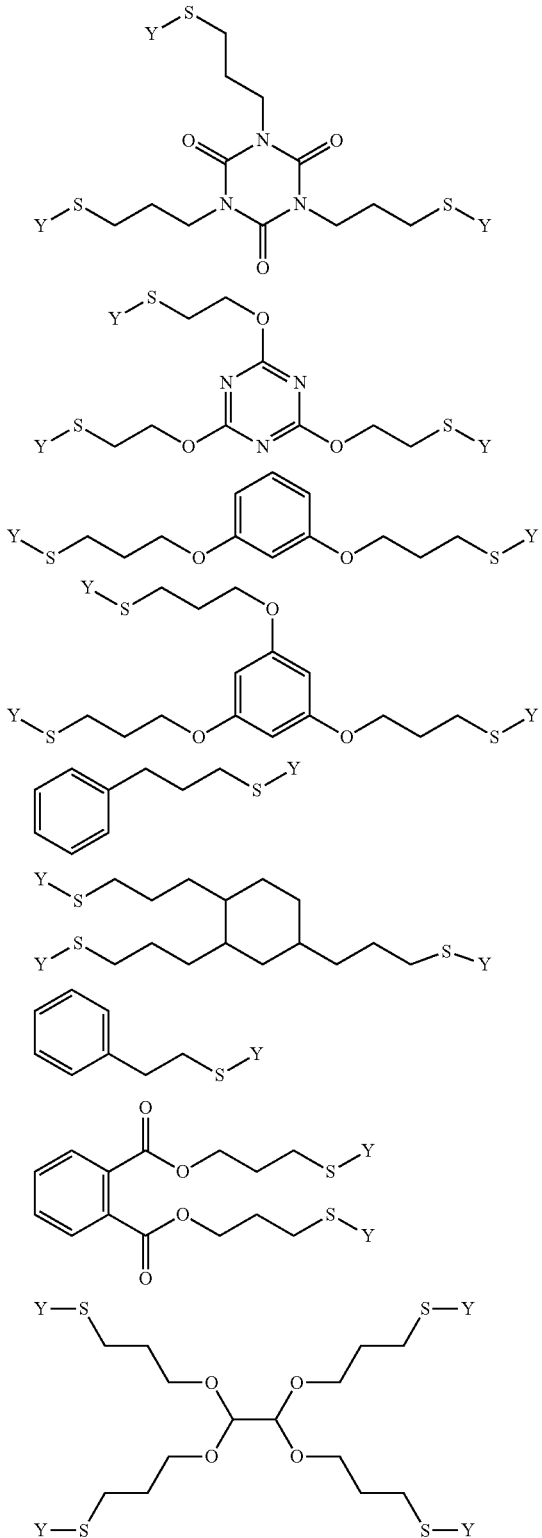

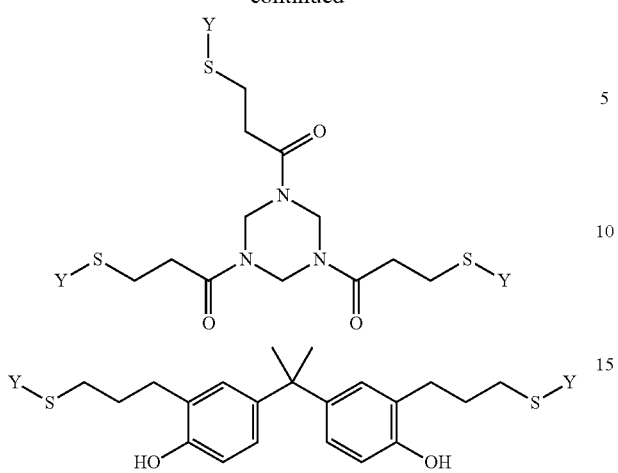

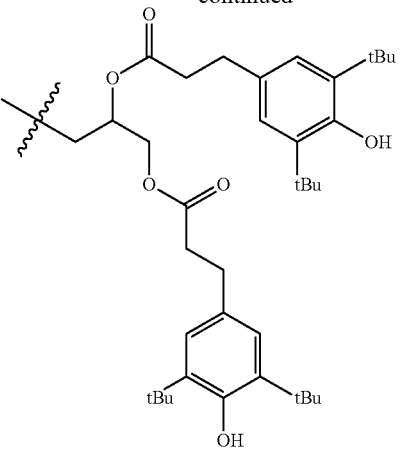

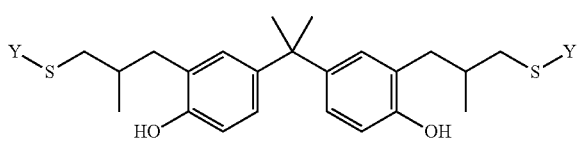

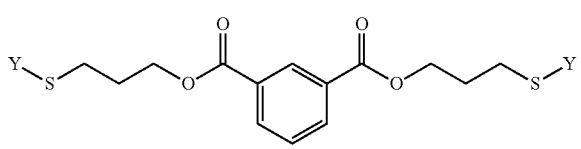

where the residue Y has the following meaning on each occurrence independently of one another:

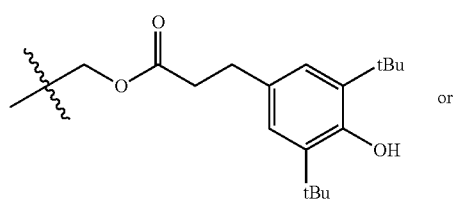 or

In the above residues, the tBu residue can also be substituted in full or in part by a methyl group and/or by hydrogen.

In addition, the present invention relates to a method of preparing a compound defined in the above and in accordance with the general formula I in which a compound in accordance with the general formula II

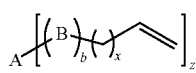

Formula II is reacted with a thiol in accordance with one of the general formulas IIIa or IIIb

Formula IIIa

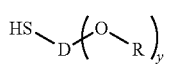

Formula IIIb and, for the case that a thiol of the general formula IIIa was used, subsequently the reaction product obtained by reaction of the compounds of formulas II and IIIa is reacted with a compound of the general formula IV

        Formula IV where
X is a leaving group; and
the meaning of the variables A, B, D, R, b, x, y, and z takes place as defined in the compounds of the formulas IIa, IIb, and III.

Reference is made to the above explanations for specific variations of the variables A, B, D, R, b, x, y, and z in the previously named formulas II, IIIa, and IIIb to avoid repetition. All of the preferred embodiments for the compound 1 in accordance with the invention apply equally to the formulas II, IIIa, IIIb, and IV.

The previously mentioned leaving group is here in particular an alcoholate, a halide, trifluoromethane sulfonate, tosylate, mesylate, fluorosulfonate, or nonaflate.

The preparation of the compounds in accordance with the invention accordingly takes place by means of a thiol-ene reaction or coupling.

The reaction of a thiol with reactive C-C double bonds takes place here.

The thiol-ene coupling is a reaction that is e.g. used for the synthesis of coatings, for the manufacture of films, and for the modification of polymers (see e.g. C. E. Hoyle, C. N. Bowman, Angew. Chem. Int. Ed. 2010, 49, 1540-1573; A. B. Lowe, Polym. Chem. 2010, 1, 17-36). The use of triallyl cyanurate, that is inter alia used as a precursor in the stabilizers in accordance with the invention is described as a starting product for the thiol-ene coupling by Z. Itintas et al. Chinese Journal of Polymer Science 2015, 6, 850-856. It serves as a thioether-functionalized chain extender in thermoplastic polyurethanes; a use as a stabilizer or as an intermediate for stabilizers is not described therein or cannot be derived therefrom. The use of diallyl phthalate, that is inter alia used as a precursor in the stabilizers in accordance with the invention, is described as a starting product for the thiol-ene coupling by Herweh et al.(U.S. Pat. No. 4,035,337) as an inhibiting agent for (aromatic) amine-induced yellowing. A molecule combination and a use with sterically hindered phenols is not described therein or cannot be derived therefrom. The use of styrene, that is inter alia likewise used as a precursor in the stabilizers in accordance with the invention, as a starting product for the thiol-ene coupling is described inter alia as a fungicide by Dazzi (U.S. Pat. No. 2,642,373) or as a plasticizer for vinyl chloride polymers by Gluesenkamp (U.S. Pat. No. 2,617,778 A), and inter alia as a photoinitiated alternative to organocatalytic thiol-olefin additions in possible peptide and glucoside modification by Limnios et. al. Adv. Synth. Catal. 2017, 359, 323- 328. A use as a stabilizer or as an intermediate for antioxidants is also not described therein or cannot be derived therefrom.

The thiol-ene reaction is mentioned in connection with stabilizers/stabilization in H. Li et al. Polymer Composites 2015 and W. Wu J. Macromol. Sci. B 2014, 53, 1244-1257. Reference is made to these documents with respect to the reaction principles that also apply to the purposes of the present invention. In the first case, the synthesis of a silane takes place via a Michael addition to an acrylate having a phenolic stabilizer function. In the second case, the reaction of a polyhydroxylated polybutadiene takes place first, with a reaction with a diisocyanate and a sterically hindered phenol subsequently taking place. The two described reactions result in different chemical products than the stabilizers in accordance with the invention.

The conversion of the compound in accordance with the general formula II with the thiol in accordance with one of the general formulas IIIa or IIIb is preferably carried out with an excess of the thiol with respect to the unsaturated function of the compound in accordance with the general formula II.

The present invention additionally relates to a composition comprising or consisting of at least one organic component to be stabilized and at least one compound in accordance with the invention in accordance with formula I as described above.

Stabilizers for thermoplastic, elastomer, and duromer plastics can in particular be formed in the form of injection molded parts, foils or films, coatings or lacquers, foams, fibers, cables and tubes, profiles, hollow bodies, ribbons, membranes, e.g. geomembranes, or adhesives that are e.g. manufactured via extrusion, injection molding, blow molding, calendering, pressing processes, spinning processes, rotomolding, or spreading and coating processes. The compositions in accordance with the invention are e.g. used for the electrical and electronic industry, the construction industry, the transport industry (automobiles, airplanes, ships, railroads), for medical applications, for domestic and electrical appliances, vehicle parts, consumer goods, packaging, furniture, or textiles. A further area of use includes lacquers, paints, and coatings as well as oils and fats such as heavy duty lubricants.

An advantageous embodiment of the present composition provides that the component to be stabilized is selected of the group comprising plastics, oils, lubricants and fats.

Suitable plastics or polymers that can be included in the composition in accordance with the invention are here in particular a) polymers of olefins or diolefins such as polyethylene (LDPE, LLDPE, VLDPE. ULDPE, MDE, HDPE, and UHMWPE), metallocene PE (m-PE), polypropylene, polyisobutylene, poly-4-methyl-pentene-1, polybutadiene, polyisoprene, polycyclooctene, polyalkylene-carbon monoxide copolymers, and copolymers in the form of statistical or block structures such as polypropylene-polyethylene (EP), EPM or EPDM, ethylene-vinyl acetate (EVA), ethylene-acrylic esters such as ethylene butyl acrylate, ethylene-acrylic acid and their salts (ionomers), and terpolymers such as ethylene acrylic acid glycidyl acrylate, graft polymers such as polypropylene g-maleic acid anhydride, polypropylene g-acrylic acid, and polyethylene g-acrylic acid, b) polystyrene, polymethylstyrene, polyvinylnaphthalene, styrene butadiene (SB), styrene butadiene styrene (SBS), styrene ethylene butylene styrene (SEBS), styrene ethylene propylene styrene, styrene isoprene, styrene isoprene styrene (SIS), acrylonitrile butadiene styrene (ABS), acrylonitrile styrene acrylate (ASA), methacrylate butadiene styrene (MBS), methacrylate acrylonitrile butadiene styrene (MABS), styrene ethylene styrene maleic acid anhydride polymers, including corresponding graft copolymers such as styrene on butadiene, and maleic acid anhydride on SBS or SEBS, c) polymers containing halides such as polyvinyl chloride (PVC), polychloroprene, and polyvinylidene chloride (PVDC), copolymers of vinyl chloride and vinylidene chloride or of vinyl chloride and vinyl acetate, chlorinated polyethylene, and polyvinylidene fluoride, d) polymers of unsaturated esters such as polyacrylates and polymethacrylates such as polymethyl methacrylate (PMMA), polybutyl acrylate, polylauryl acrylate, poly stearyl acrylate, polyacrylonitrile, polyacrylamides, and copolymers such as polyacrylonitrile-poly alkyl acrylate, e) polymers of unsaturated alcohols and derivatives such as polyvinyl alcohol, polyvinyl acetate, and polyvinyl butyral, f) polyacetates such as polyoxymethlyene (POM) or copolymers with e.g, butanal, g) polyphenylene oxides and blends with polystyrene or polyamides, h) polymers of cyclic ethers such as polyethylene glycol, polypropylene glycol, polyethylene oxide, and polypropylene oxide, i) polyurethanes of hydroxy terminated polyethers or polyesters and aromatic or aliphatic isocyanates, in particular linear polyurethanes and polyureas, j) polyamides such as polyamide-6, 6.6, 6.10, 4.6, 4.10, 6.12, 12.12, polyamide 11, polyamide 12 and (partly) aromatic polyamides such as polyphthalamides, e.g. prepared from terepththalic acid and/or isophthalic acid and aliphatic diamines or from aliphatic dicarboxylic acids such as adipic acid or sebacic acid and aromatic diamines such as 1,4- or 1,3-diaminobenzol, k) polyimides, polyamide imides, polyether imides, polyester imides, poly(ether) ketones, polysulfones, polyether sulfones, polyaryl sulfones, polyphenylene sulfide, polybenzimidazoles, and polyhydantoins, l) polyesters of aliphatic or aromatic dicarboxylic acids and diols or of hydroxy carboxylic acids such as polyethylene terephthalate (PET), polybutylene terephthalate (PBT), polypropylene terephthalate, poly-1,4-dimethylol cyclohexane terephthalate, polyhydroxy benzoate, polyhydroxy naphthalate, and polylactic acid, m) polycarbonates, polyester carbonates, and blends such as PC/ABS, PC/PBT, and PC/PET/PBT, n) cellulose derivatives such as cellulose nitrate, cellulose acetate, cellulose propionate, and cellulose butyrate, o) non-thermoplastic plastics or duroplastics p) and mixtures, combinations, or blends of two or more of the above-named polymers.

If the above-named polymers are copolymers, they can be present in the form of statistical (random) block structures or tapered structures or as stereo block copolymers.

If they are stereoregular polymers; they can be present in the form of isotactic, stereotactic, but also atactic forms.

The polymers may also be present in cross-linked form. A cross-linking can here e.g. take place by the addition of radical formers or by radiation such as electron rays, beta rays, or gamma rays during processing or in a following step.

Said polymers can here not only be present as new products, but also in the form of recycled products, e.g. as production waste or from collections of recyclables (post-consumer recycled products).

The present compounds can furthermore be used for the stabilization of rubbers and elastomers. It can here be a case of natural rubber (NR) or synthetic rubber materials.

It is preferred with respect to the contained quantities of the compound in accordance with formula I if the composition comprises or consists of 95.00 to 99.99 wt %, preferably 97.00 to 99.95 wt %, particularly preferably 98.00 to 99.90 wt %, of at least one component to be stabilized and 0.01 to 5.00 wt %, preferably 0.05 to 3.00 wt %, particularly preferably 0.10 to 2.00 wt %, of at least one compound in accordance with the invention in accordance with the general formula I.

The composition in accordance with the invention, e.g. on the basis of plastics, can additionally comprise at least one additive. This at least one additive is in particular selected from the group comprising UV absorbers, light stabilizers, stabilizers, antioxidants, hydroxyl amines, benzofurans, metal deactivators, filler deactivators, antiozonants, nucleation agents, impact strength improvers, plasticizers, lubricants, rheology modifiers, thixotropic agents, chain extenders, processing aids, demolding aids, flame retardants, pigments, dyes, optical brighteners, antimicrobial agents, antistatic agents, slip agents, antiblocking agents, coupling agents, crosslinking agents, anti-crosslinking agents, hydrophilization agents, hydrophobization agents, bonding agents, dispersion agents, degradation additives, defoaming aids, odor traps, marking agents, antifogging agents, fillers, and reinforcements.

Suitable light stabilizers are, for example, compounds based on 2-(2'-hydroxyphenyl) benzotriazoles, 2-hydroxy benzophenones, esters of benzoic acids, acrylates, oxamides, and 2-(2-hydroxyphenyl)-1,3,-5-triazines.

Suitable 2-(2'-hydroxyphenyl) benzotriazoles are, for example, 2-(2'-hydroxy-5'methylphenyl) benzotriazole, 2-(3',5'-di-tert-butyl-2'-hydroxyphenyl) benzotriazole, 2-(5'-Cert-butyl-2'-hydroxy-phenyl) benzotriazole, 2-(2'-hydroxy-5'-(1,1,3,3-tetramethylbutyl) phenyl) benzotriazole, 2-(3',5'-di-tert-butyl-2'-hydroxyphenyl)-5-chlorobenzotriazole, 2-(3'-tert-butyl-2'-hydroxy-5'-methylphenyl-5-chlorobenzotriazole, 2-(3'-sec-butyl-5'-ter-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis(α,α-dimethylbenzyl)-2'-hydroxyphenyl) benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)-5-benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy) carbonylethyl]-2'-hydroxyphenyl) benzotriazole, 2-(3'-dodecyl-2'-hydroxy-5'-methylphenyl) benzotriazole, 2-(3'-tert-butyl-2'-hydroxy-5'-(2-isooctyloxycarbonylethyl) phenylbenzotriazole, 2,2'-methylenebis[4-(1,1,3,3-tetramethylbutyl)-6-benzotriazole-2-ylphenol]; the product of the transesterification of 2-[3'-tert-butyl-5'-(2-methoxycarbonylethyl)-2'-hydroxyphenyl]-2H-benzotriazole with polyethylene glycol 300; $[R—CH_2CH_2—COO—CH_2CH_2—]_2$, where R=3'-tert-butyl-4'-hydroxy-5'-2H-benzotriazole-2-ylphenyl, 2-[2'-hydroxy-3'-(α,α-dimethylbenzyl)-5'-(1,1,3,3-tetramethylbutyl)phenyl] benzotriazole, 2-[2'-hydroxy-3'-(1,1,3,3-tetramethylbutyl)-5'-(α,α-dimethylbenzyl)phenyl] benzotriazole.

Suitable 2-hydroxybenzophenones are, for example, 4-hydroxy-, 4-methoxy-, 4-octyloxy-, 4-decyloxy, 4-dodecyloxy, 4-benzyloxy, 4,2',4'-trihydroxy- and 2'-hydroxy-4,4'-dimethyoxy derivatives of the 2-hydroxy benzophenones.

Suitable acrylates are, for example, ethyl-α-cyano-β,β-diphenylacrylate, isooctyl-α-cyano-β, β-diphenylacrylate, methyl-α-carbomethoxycinnamate, methyl-α-cyano-β-methyl-α-methoxycinnamate, butyl-α-cyano-β-methyl-p-methoxycinnamate, methyl-α-carbomethoxy-p-methoxycinnamate and N-(β-carbomethoxy-β-cyanovinyl)-2-methylindoline.

Suitable esters of benzoic acids are, for example, 4-tert-butylphenyl salicylate, phenylsalicylate, octylphenylsalicylate, dibenzoyl resorcinol, bis(4-tert-butylbenzoyl)resorcinol, benzoyl resorcinol, 2,4-di-tert-butylphenyl-3,5-di-tert-butyl-4-hydroxybenzoate, hexadecyl-3,5-di-tert-butyl-4-hydroxybenzoate, octadecyl-3,5-di-tert-butyl-4-hydroxybenzoate, 2-methyl-4,6-di-tert-butylphenyl-3,5-di-tert-butyl-4-hydroxybenzoate.

Suitable oxamides are, for example, 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl) oxamide, 2-ethoxy-5-tert-butyl-2'-ethoxanilide and its mixtures with 2-ethoxy-2'-ethyl-5,4'-di-Cert-butoxanilide, mixtures of o- and p-methoxy-disubstituted oxanilides and mixtures of o- and p-ethoxy-disubstituted oxanilides.

Suitable 2-(2-hydroxyphenyl)-1,3,5-triazines are, for example, 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl-1, 3,5-triazine, 2-(2-hydroxy-4-dodecyloxyphenyl)-4,6-bis(2, 4-dimethylphenyl)-1,3,5-triazine, 2-(2-hydroxy-4-tridecy-loxyphenyl)-4,6-bis(2,4-dimethylphenyl)-1,3,5-triazine, 2-[2-hydroxy-4-(2-hydroxy-3-butyloxypropoxy)-phenyl]-4, 6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-do-decyloxypropoxy)phenyl]-4,6-bis(2,4-dimethylphenyl-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-12-hydroxy-4-[3-(2-ethylhexyl-1-oxy)-2-hydroxypropyloxy]phenyl1-4,6-bis(2,4-dimethylphenyl-1,3,5-triazine.

Suitable metal deactivtors are, for example, N,N'-diphe-nyloxamide, N-salicylal-N'-salicyloylhydrazine, N,N'-bis (salicyloyl)hydrazine, N,N'-bis(3,5-di-tert-butyl-4-hydroxy-phenylpropionyl)hydrazine, 3-salicyloylamino-1,2,4-triazole, bis(benzylidene)oxalyldihydrazide, oxanilide, isophthaloyldihydrazide, sebacoyl-bis-phenylhydrazide, N,N'-diacetyladipoyldihydrazide, N,N'-bis(salicyloyl)oxy-lyldihydrazide, N,N'-bis(salicyloyl)thiopropionyldihydrazide.

Suitable phenolic antioxidants are, for example:

Alkylated monophenols, such as 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-diocta-decyl-4-methylphenol, 2,4,6-tricyclohexylphenol, 2,6-di-tert-butyl-4-methoxymethylphenol, linear or branched non-ylphenols such as 2,6-dinonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof;

alkylthio methylphenols such as 2,4-dioctylthiomethyl-6-tert-butylphenol, 2,4-dioctylthiomethyl-6-methylphenol, 2,4-dioctylthiomethyl-6-ethylphenol, and 2,6-didodecylth-iomethyl-4-nonylphenol;

hydroquinones and alkylated hydroquinones such as 2,6-di-tert-butyl-4-methoxyphenol, 2,5-di-tert-butylhydrocqui-none, 2,5-di-tert-amylhydroquinone, 2,6-diphenyl-4-octa-decyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenylstearate, and bis(3,5-di-tert-butyl-4-hydroxylphenyl)adipate;

tocopherols such as α-, β-, γ-, δ-tocopherol and mixtures thereof (vitamin E);

hydroxylated thiodiphenylether such as 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-am-ylphenol), 4,4'-bis(2,6-dimethyl-4-hydroxyphenyl)disulfide;

alkylide bisphenols such as 2,2'methylenebis(6-tert-butyl-4-methylphenol), 2,2'-methylenebis(6-tert-butyl-4-eth-ylphenol), 2,2'-methylenebis[4-methyl-6-(a-methylcyclo-hexyl)phenol], 2,2'-methylenebis(4-methyl-6-cyclhexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethyliden-ebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol, 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethyleneglycol-bis[3,3-bis(3'-tert-butyl-4'-hydroxyphenyl) butyrate], bis(3-tert-butyl-4-hydroxy-5-methylphenyl)dicy-clopentadiene, bis[2-(3'-tert-butyl-2'-hydroxy-5'-methylben-zyl)-6-tert-butyl-4-methylphenyl]terephthalate, 1,1-bis-(3, 5-dimethyl-2-hydroxyphenyl)butane, 2,2-bis(3,5-di-tert-butyl-4-hydroxyphenyl)propane, 2,2-bis-(5-tert-butyl-4-hydroxy-2-methylphenyl)-4-n-dodecylmercaptobutane, 1,1, 5,5-tetra(5-tert-butyl-4-hydroxy-2-methylphenyl)pentane;

O-, N- and S-benzyl compounds such as 3,5,3',5'-tetra-tert-butyl-4,4'-dihydroxydibenzylether, octadecyl-4-hy-droxy-3,5-dimethylbenzylmercaptoacetate, tridecyl-4-hy-droxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, and isooctyl-3,5-di-tert-butyl-4-hydroxybenzylmercaptoacetate;

hydroxybenzylated malonates such as dioctadecyl-2,2-bis (3,5-di-tert-butyl-2-hydroxybenzyl)malonate, dioctadecyl-2-(3-tert-butyl-4-hydroxy-5-methylbenzyl)malonate, dido-decylmercaptoethyl-2,2-bis(3,5-di-tert-butyl-4-hydroxybenzyl)malonate, and bis[4-(1,1,3,3-tetramethylbutyl)phenyl]-2,2-bis(3,5-di-tert-butyl-4-hydroxybenzyl)malonate;

aromatic hydroxybenzyl compounds such as 1,3,5-tris(3, 5-di-tert-butyl-4-hydroxybenzyl)-2,4,6-trimethylbenzene, 1,4-bis(3,5-di-tert-butyl-4-hydroxybenzyl)-2,3,5,6-tetram-ethylbenzene, and 2,4,6-tris(3,5-di-tert-butyl-4-hydroxyben-zyl)phenol;

triazine compounds such as 2,4-bis(octylmercapto)-6-(3, 5-di-tert-butyl-4-hydroxyanilino)-1,3,5-triazine, 2-octyl-mercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris(3,5-di-tert-butyl-4-hydroxybenzyl)iso-cyanurate, 1,3,5-tris(4-tert-butyl-3-hydroxy-2,6-dimethylbenzypisocyanurate, 2,4,6-tris(3,5-di-tert-butyl-4-hydroxphenylethyl)-1,3,5-triazine, 1,3,5-tris(3,5-di-tert-butyl-4-hydroyphenylpropionyl)hexa-hydro-1,3,5-triazine, 1,3,5-tris(3,5-dicyclohexyl-4-hydroxybenzyl)isocyanurate;

benzylphosphonates such as dimethyl-2,5-di-tert-butyl-4-hydroxybenzylphosphonate, dietyh1-3,5-di-tert-butyl-4-hy-droxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethylester of the 3,5-di-tert-butyl-4-hydroxyben-zylphosphonic acid;

acylaminophenols such as 4-hydroxylauranilide, 4-hy-droxystearanilide, octyl-N-(3,5-di-tert-butyl-4-hydroxyphe-nyl)carbamate;

esters of the β-(3-(3,5-Di-tert-butyl-4-hydroxyphenyl) propionic acid with monovalent or polyvalent alcohols, e.g. methanol, ethanol, n-octanol, i-octanol, octadecanol, 1,6-hexanediol, 1,9-nonanediol, ethyleneglycol, 1,2-propane-diol, neopentylglycol, thiodiethyleneglycol, diethylenegly-col, triethyleneglycol, pentaerythritol, tris(hydroxyethyl) isocyanurate, N,N'-bis(hydroxyethyl)oxamied, 3-thiaundecanol, 3-thiapentadecanol, trimethylhexanediol, trimethylolpropane, 4-hydroxymethyl-1-phospha-2,6,7-tri-oxabicyclo[2.2.2]octane;

esters of the β-(5-tert-butyl-4-hydroxy-3-methylphenyl) propionic acid with monovalent or polyvalent alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethyleneglycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane, 3,9-bis[2-{3-(3-tert-butyl-4-hydroxy-5-methylphenyl)-propionyloxy}-1,1-dimethylethyl]-2,4,8,10-tetraoxaspiro[5.5]undecane;

esters of the β-(3,5-dicyclohexyl-4-hydroxyphenyl)propionic acid with monovalent or polyvalent alcohols such as methanol, ethanol, octanol, octadecanol, 1,6-hexanediol, 1,9-nonanediol, ethyleneglycol, 1,2-propanediol, neopentylglycol, thiodiethyleneglycol, diethyleneglycol, triethyleneglycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane;

esters of the (3,5-di-tert-butyl-4-hydroxyphenyl)acetic acid with monovalent or polyvalent alcohols, e.g. methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)-oxamide, 3-thiaundecanol, 3-Thiapentadecanol, trimethylhexanediol, trimethylolpropane, 4-hydroxymethyl-1-phospha-2,6,7-trioxa bicyclo[2.2.2]octane;

amides of the β-(3,5-di-tert-butyl-4-hydroxyphenyl)propionic acid such as N,N'-bis(3,5-di-tert-butyl-4-hydroxyphenylpropionyl)hexamethylene diamide, N,N'-bis(3,5-di-tert-butyl-4-hydroxyphenylpropionyl)hexamethylene diamide, N,N'-bis(3,5-di-tert-butyl-4-hydroxyphenylpropionyl)hexamethylene diamide, N,N'-bis(3,5-di-tert-butyl-4-hydroxyphenylpropionyl)hydrazide, N, N'-bis[2-[3,5-di-tert-butyl-4-hydroxyphenyl]propionyloxy)ethyl]oxamide (Naugard®XL-1, marketed by Uniroyal);

ascorbic acid (vitamin C).

Particularly preferred phenolic antioxidants include:
octadecyl-3-(3,5-di-tert-butyl-4-hydroxyphenyl)propionate, pentaerythritol-tetrakis[3-(3,5-di-tert-butyl-4-hydroxyphenyl]propionate, tris(3,5-di-tert-butyl-4-hydroxyphenyl)isocyanurate, 1,3,5-trimethyl-2,4,6-tris(3,5-di-tert-butyl-4-hydroxyphenyl)isocyanurate, 1,3,5-trimethyl-2,4,6-tris(3,5-di-tert-butyl-4-hydroxy-benzyl)benzol, triethylene glycol-bis[3-(3-tert-butyl-4-hydroxy-5-methylphenyl)propionate, N,N'-hexane-1,6-diyl-bis[3-(3,5-di-tert-butyl-4-hydroxyphenyl)propionic acid amide.

Suitable phosphites/phosponites are, for example:
triphenylphosphite, diphenylalkylphosphites, phenyldialkylphosphites, tri(nonylphenyl)phosphite, trilaurylphosphites, trioctadecylphosphite, distearylpentaerythritoldiphosphite, tris-(2,4-di-tert-butylphenyl phosphite, diisodecylpentaerythritoldiphosphite, bis(2,4-di-tert-butylphenyl)penta-erythritoldiphosphite, bis(2,4-di-cumylphenyl)pentaerythritoldiphosphite, bis(2,6-di-tert-butyl-4-methylphenyl)pentaerythritoldiphosphite, diisodecyloxypentaerythritoldiphosphite, bis(2,4-di-tert-butyl-6-methylphenyl)pentaerythritoldiphosphite, bis(2,4,6-tris(tert-butylphenyl)pentaerythritoldiphosphite, tristearylsorbitoltriphosphite, tetrakis(2,4-di-tert-butylphenyl)-4,4'-biphenylene diphosphonite, 6-isooctyloxy-2,4,8,10-tetra-tert-butyl-12H-dibenz[d,g]-1,3,2-dioxaphosphocine, bis(2, 4-di-tert-butyl-6-methylphenyl)methylphosphite, bis(2,4-di-tert-butyl-6-methylphenyl)ethylphosphite, 6-fluoro-2,4,8, 10-tetra-tert-butyl-12-methyl-dibenz[d,g]-1,3,2-dioxaphosphocine, 2,2'2"-nitrilo[triethyltris(3,3",5,5'T-tetra-tert-butyl-1,1'-biphenyl-2,2T-diyl)phosphite], 2-ethylhexyl (3,3',5,5'T-tetra-tert-butyl-1,1T-biphenyl-2,2'T-diyl)) phosphite, 5-butyl-5-ethyl-2-(2,4,6-tri-tert-butylphenoxy)-1,3,2-dioxaphosphirane.

Particularly preferred phosphites/phosphonites are:

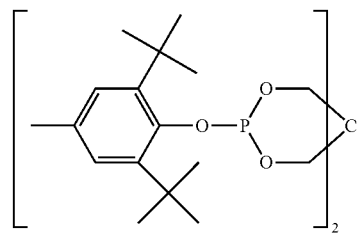

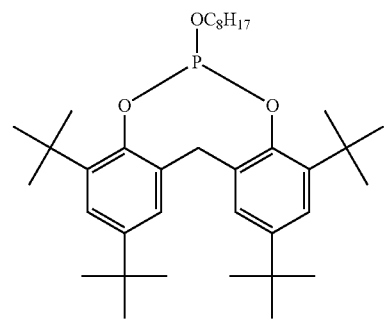

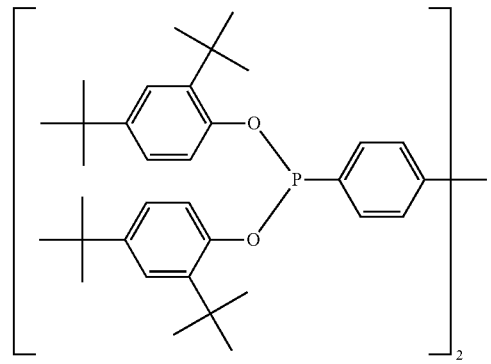

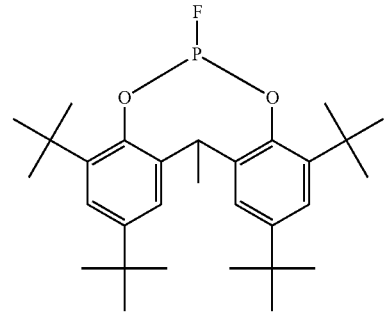

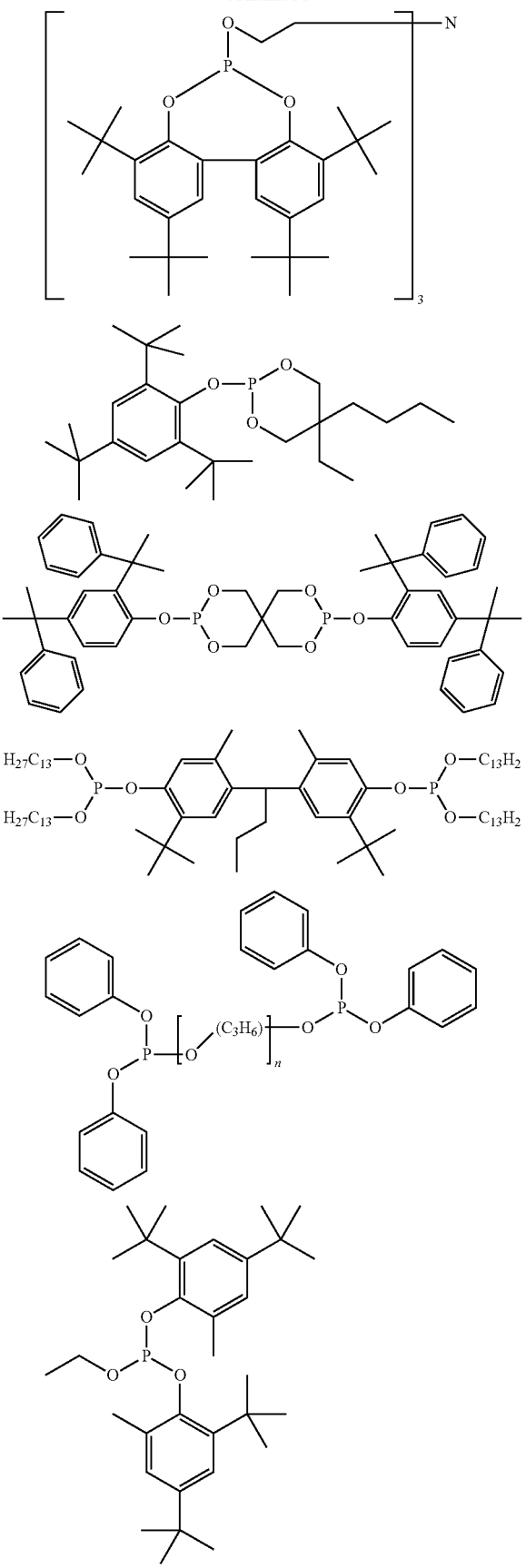

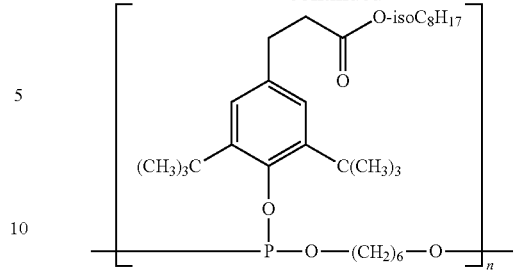

where n can be between 1 and 100.

Further suitable stabilizers are aminic antioxidants.

Suitable aminic antioxidants are, for example: N,N'-di-isopropyl-p-phenylene diamine, N,N'-di-sec-butyl-p-phenylene diamine, N,N'-bis(1,4-dimethylpentyl)-p-phenylene diamine, N,N'-bis(1-ethyl-3-methylpentyl)-p-phenylene diamine, N,N'-bis(1-methylheptyl)-p-phenylene diamine, N,N'-dicyclohexyl-p-phenylene diamine, N,N'-diphenyl-p-phenylene diamine, N,N'-bis(2-naphthyl)-p-phenylene diamine, N-isopropyl-N'-phenyl-p-phenylene diamine, N-(1,3-dimethylbutyl)-N'-phenyl-p-phenylene-diamine, N-(1-methylheptyl)-N'-phenyl-p-phenylene diamin, N-cyclohexyl-N'-phenyl-p-phenylene diamine, 4-(p-toluenesulfamoyl)diphenylamine, N,N'-dimethyl-N,N'-di-sec-butyl-p-phenylene diamine, Diphenylamine, N-allyldiphenylamine, 4-isopropoxydiphenylamine, N-phenyl-1-naphthylamine, N-(4-tert-octylphenyl)-1-naphthylamine, N-phenyl-2-naphthyl-amine, octylated diphenylamine, e.g. p,p'-di-tert-octyldiphenylamine, 4-n-butylaminophenol, 4-butyrylaminophenol, 4-nonanoylaminophenol, 4-dodecanoyl-aminophenol, 4-octadecanoylamino-phenol, bis(4-methoxyphenyl)amine, 2,6-di-tert-butyl-4-dimethylaminomethyl-phenol, 2,4'-diaminodiphenylmethane, 4,4'-diaminodiphenylmethane, N,N,N',N'-tetra-methyl-4,4'-diaminodiphenylmethane, 1,2-bis[(2-methyl-phenyl)amino]ethane, 1,2-bis(phenylamino)propane, (o-tolyl)biguanide, bis[4-(1',3T-dimethylbutyl)phenyl]amine, tert-octylated N-phenyl-1-naphthylamine, a mixture of mono-alkylated and dialkylated tert-butyl/tert-octyldiphenylamines, a mixture of monoalkylated and dialkylated nonyldiphenylamines, a mixture of monoalkylated and dialkylated dodecyl-diphenylamines, a mixture of monoalkylated and dialkylated isopropyl/isohexyl-diphenylamines, a mixture of monoalkylated and dialkylated Cert-butyldiphenylamines, 2,3-dihydro-3,3-dimethyl-4H-1,4-benzothiazine, phenothiazine, a mixture of monoalkylated and dialkylatedvtert-butyl/tert-octylphenothiazines, a mixture of monoalkylated and dialkylated tert-octylphenothiazines, N-allylphenothiazine, N,N,N',N'-tetraphenyl-1,4-diaminobut-2-ene and mixtures or combinations hereof.

Preferred aminic antioxidants include: N,N'-di-isopropyl-p-phenylene diamine, N,N'-di-sec-butyl-p-phenylene diamine, N,N'-bis(1,4-dimethylpentyl)-p-phenylene diamine, N,N'-bis(1-ethyl-3-methylpentyl)-p-phenylene diamine, N,N'-bis(1-methylheptyl)-p-phenylene diamine, N,N'-dicyclohexyl-p-phenylene diamine, N,N'-diphenyl-p-phenylene diamine, N,N'-bis(2-naphthyl)-p-phenylene diamine, N-isopropyl-N'-phenyl-p-phenylene diamine, N-(1,3-dimethylbutyl)-N'-phenyl -p-phenylene-diamine, N-(1-methylheptyl)-N'-phenyl-p-phenylene diamine, N-cyclohexyl-N'-phenyl-p-phenylene diamine.

Further preferred aminic antioxidants are hydroxylamines or N-oxides (nitrons) such as N,N-dialkylhydroxylamines, N,N-dibenzylhydroxylamine, N,N-dilaurylhydroxylamine, N,N-distearylhydroxylamine, N-benzyl-α-phenylnitron, N-octadecyl-α-hexadecylnitron, and Genox EP (Addivant) in accordance with the formula:

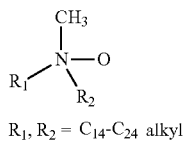

$R_1, R_2 = C_{14}-C_{24}$ alkyl

Further suitable stabilizers are thiosynergists.

Suitable thiosynergists are, for example, distearylthiodipropionate, dilaurylthiodipropionate; ditridecyldithiopropionate, ditetradecylthiodipropionate, 3-(dodecylthio)-, 1,1'-[2,2-bis[[3-(dodecylthio)-1-oxopropoxy]methyl]-1,3-propanediyl]propanoic acid ester.

Further suitable stabilizers, in particular for poylamides, are copper salts such as copper-(1)-iodide, copper-(I) bromide, or copper complexes such as triphenylphosphine copper-(I) complexes.

Further suitable stabilizers are benzofuranones and indolinones such as 3-(4-(2-acetoxyethoxy)phenyl]-5,7-di-tert-butyl-benzofuran-2-one, 5,7-di-tert-butyl-344-(2-stearoyloxyethoxy)phenyl]benzofuran-2-one, 3,3'-bis[5,7-di-tert-butyl-3-[4-(2-hydroxyethoxy]phenyl)benzofuran-2-one), 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

Suitable hindered amines are, for example 1,1-bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl)-n-butyl-3,5-di-tert-butyl-4-hydroxybenzylmalonaet, the condensation product from 1-(2-hydroxyethyl)-2,2,6,6-tetramethyl-4-hydroxypiperidine and succinic acid, linear or cyclic condensation products of N,N'-bis(2,2,6,6-tetramethyl-4-piperidyl)hexamethylene diamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane tetracarboxylate, 1,1'-(1,2-ethandiyl)-bis(3,3,5,5-tetramethylpiperazinone), 4-benzoyl-2,2,6,6-tetramethylpiperidine, 4-stearyloxy-2,2,6,6-tetramethylpiperidine, linear or cyclic condensation products of N,N'-bis (2,2,6,6-tetramethyl-4-piperidyl)hexamethylene diamine and 4-morpholino-2,6-dichloro-1,3,5-triazine, the reaction product of 7,7,9,9-tetramethyl-2-cycloundecyl-1-oxa-3,8-diaza-4-oxospiro-[4,5]decane and epichlorhydrine.

Oligomeric and polymeric hindered amines of the following structures are preferred:

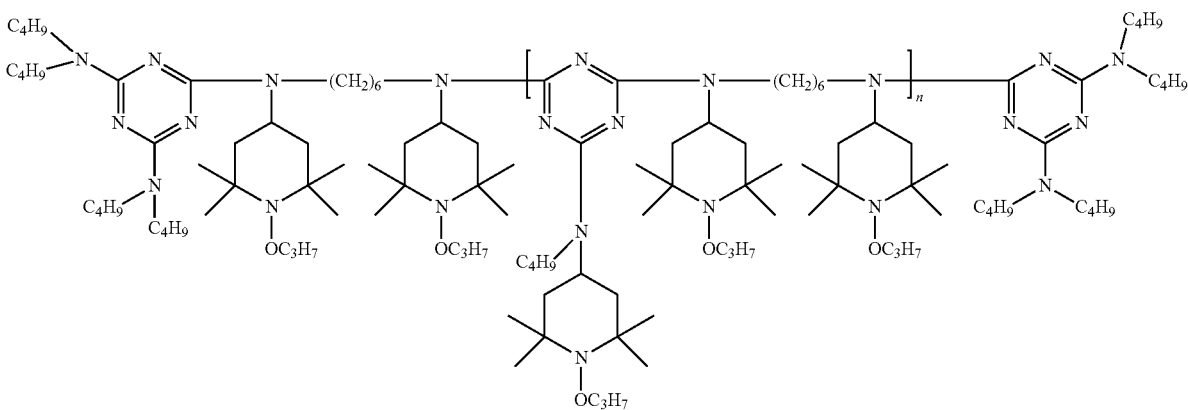

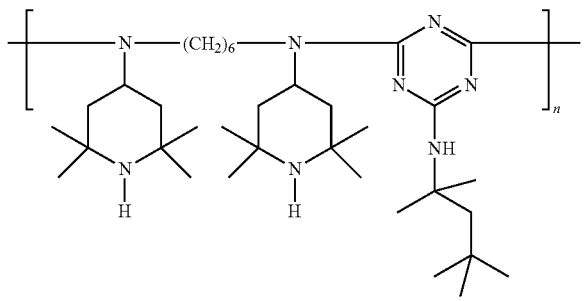

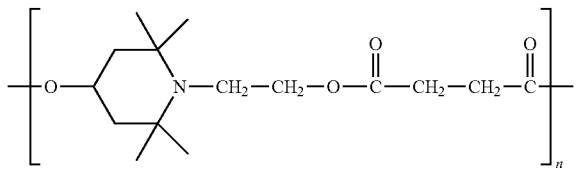

-continued
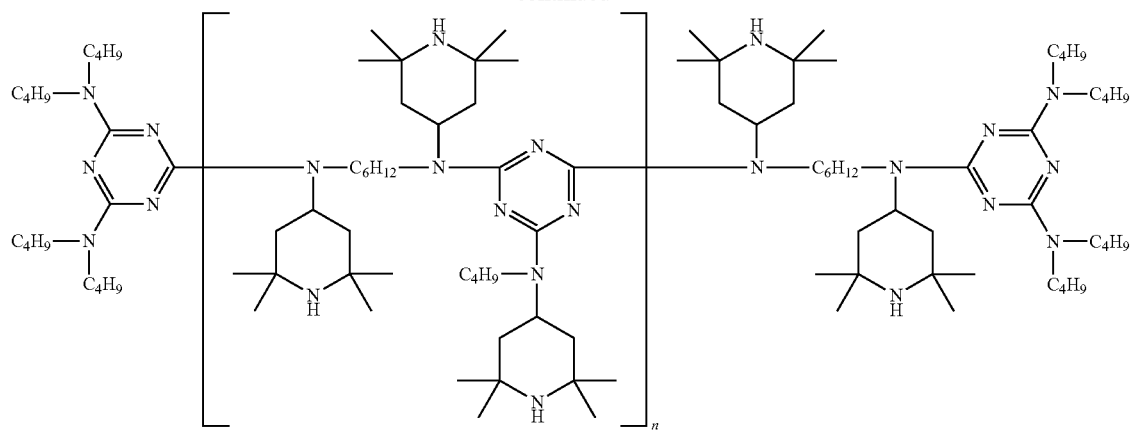
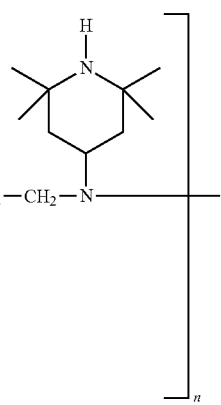
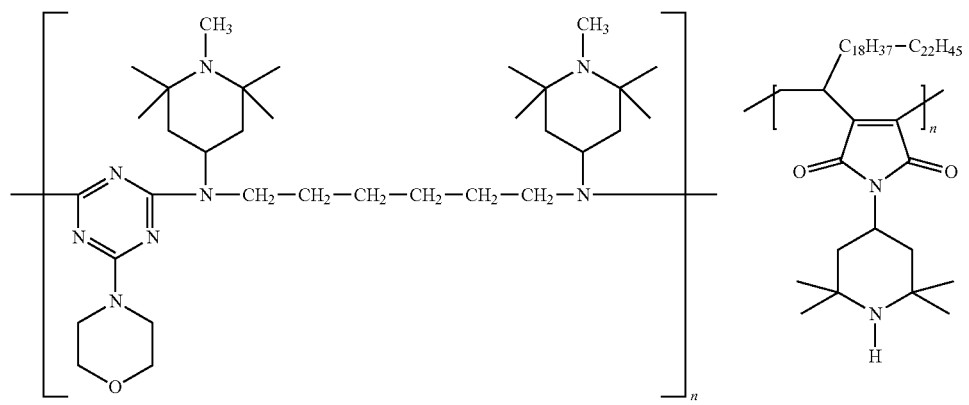
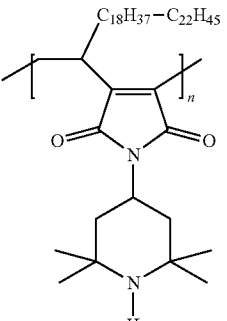

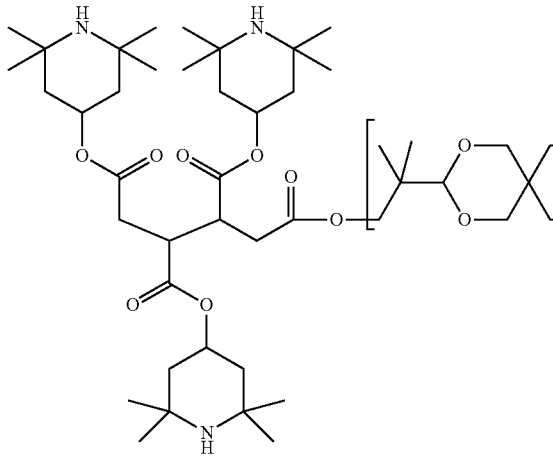 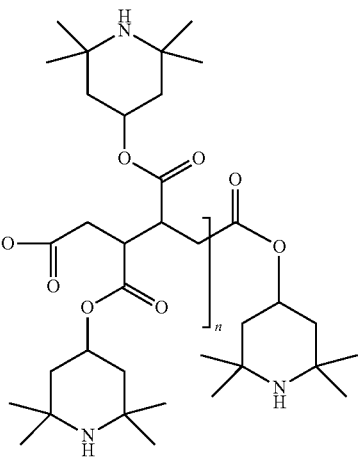

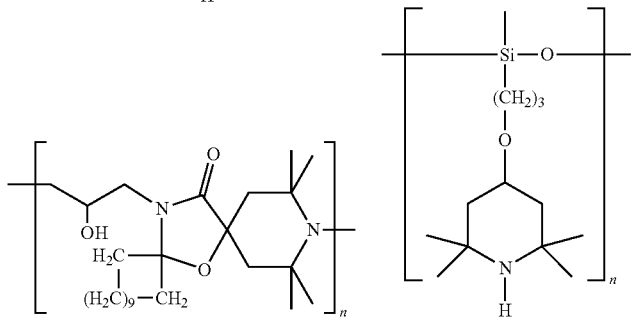

In the above-named compounds, n respectively means 3 to 100.

Suitable dispersion agents are, for example:

polyacrylates, e.g. copolymers with long-chain side groups, polyacrylate block copolymers, alkylamides: e.g. N,N'-1,2-ethanediylbisoctadecanamide sorbitan ester, e.g. monostearylsorbitan esters, titanates and zirconates, reactive copolymers having functional groups, e.g. polypropylene-co-acrylic acid, polypropylene-co-maleic acid anhydride, polyethylene-co-glycidylmethacrylate, polystyrene-alt-maleic acid anhydride-polysiloxanes: e.g. dimethylsilanodiole-ethylene-oxide copolymers, polyphenylsiloxane copolymers, amphiphilic copolymers: e.g. polyethylene-block-polyethylene oxide, dendrimers, e.g. dendrimers containing hydroxyl groups.

Suitable nucleation agents are, for example, talcum, alkali or alkaline earth salts of monofunctional and polyfunctional carboxylic acids such as benzoic acid, succinic acid, adipic acid, e.g. sodium benzoate, zinc glycerolate, aluminum hydroxy-bis(4-tert-butyl)benzoate, benzylidene sorbitols such as 1,3:2,4-bis(4-methylbenzylidene)sorbitol, 2,2'-methylene-bis-(4,6-di-tert-butylphenyl)phosphate, and tris-amides and diamides such as trimesic acid tricyclohexylamide, trimesic acid tri(4-methylcyclo-hexylamide), trimesic acid tri(tert-butylamide), N,N',N'''-1,3,5-benzoltriyltris(2,2-dimethyl-propanamide) or 2,6-naphthalindicarboxylic acid-cyclohexylamide.

Suitable antinucleation agents are azine dyes such as nigrosin.

Suitable flame retardant agents are, for example:
a) Inorganic flame retardant agents such as Al(OH)$_3$, Mg(OH)$_2$, AlO(OH), MgCO$_3$, sheet silicates such as montmorillonite or sepiolite, unmodified or organically modified double salts such as Mg-Al-silicates, POSS (polyhedral oligomeric silsesquioxanes) compounds, huntite hydromagnesite or halloysite and Sb$_2$O$_3$, Sb$_2$O$_5$, MoO$_3$, zinc stannate, zinc hydroxystannate,
b) flameproofing agents containing nitrogen such as melamine, melem, melam, melon, melamine derivatives, melamine condensation products or melamine salts, benzoguanamine, polyisocyanurates, allantoin, phosphacenes, in particular melamine cyanurate, melamine phosphate, dimelamine phosphate, melamine pyrophosphate, melamine polyphosphate, melamine metal phosphates such as melamine aluminum phosphate, melamine zinc phosphate, melamine magnesium phosphate, and the corresponding pyrophosphates and polyphosphates, poly-[2,4-(piperazine-1,4-yl)-6-(morpholine-4-yl)-1,3,5-triazine], ammonium polyphosphate, melamine borate, melamine hydrobromide,
c) radical formers such as alkoxyamines, hydroxylamine esters, azo compounds, dicumyl or polycumyl, hydroxyimides and their derivatives such as hydroxyimide esters or hydroxyimide ethers,
d) Flame retardant agents containing phosphorus such as red phosphorus, phosphates such as resorcin diphosphte, bisphenol-A-diphosphate, and their oligomers, triphenylphosphate, ethylene diamine diphosphate, phosphinates such as salts of the hypophosphorous acid and their derivatives such as alkylphosphinate salts, e.g. diethylphosphinate aluminum or diethylphosphinate zinc or aluminum phosphinate, aluminum phosphite, aluminum phosphonate, phosphonate esters, oligomer and polymer derivatives of the methane phosphonic acid, 9,10-dihydro-9-oxa-10-phosphorylphenanthrene-10-oxide (DOPO) and their substituted compounds,
e) halogenated flameproofing agents based on chlorine and bromine such as polybrominated diphenyl oxides such as decabromodiphenyloxide, tris(3-bromo-2,2-bis(bromomethyl)propyl-phosphate, tris(tribromoneopentyl)phosphate, tetrabromophthalic acid, 1,2-bis(tribromophenoxy)ethane, hexabromocyclo-dodecane, brominated diphenylethane, tris-(2,3-dibrompropyl) isocyanurate, ethylene-bis-(tetrabromophthalimide), tetrabromo-bisphenol A, brominated polystyrene, brominated polybutadiene or polystyrene brominated polybutadiene copolymers, brominated polyphenylene ether, brominated epoxy resin, polypentabromobenzylacrylate, optionally in combination with $Sb_2O_3$ and/or $Sb_2O_5$,
f) borates such as zinc borate or calcium borate, optionally on a carrier material such as silica.
g) compounds containing sulfur such as elemental sulfur, disulfides and polysulfides, thiuram sulfide, dithiocarbamates, mercaptobenzthiazole and sulfene amides,
h) anti-drip agents such as polytetrafluorethylene,
i) compounds containing silicon such as polyphenylsiloxanes,
j) carbon modifications such as carbon nanotubes (CNTs), expanded graphite, or graphene
and combinations or mixtures thereof.

Suitable fillers and reinforcements are, for example, synthetic or natural material such as calcium carbonate, silicates, glass fibers, glass spheres (solid or hollow), talcum, micra, kaolin, barium sulfate, metal oxides and metal hydroxides, black carbon, graphite, carbon nanotubes, graphene, wood flour, or fibers of natural products such as cellulose or synthetic fibers. Further suitable fillers include hydrotalcites or zeolites or phyllosilicates such as montmorillonite, bentonite, beidellite, mica, hectorite, saponite, vermiculite, ledikite, magadite, illite, kaolinite, wollastonite, attapulgite.

Suitable pigments can be of an inorganic or organic nature. Inorganic pigments are, for example, titanium dioxide, zinc oxide, zinc sulfide, iron oxide, ultramarine, black carbon; organic pigments are, for example, anthraquinones, anthanthrones, benzimidazolones, chinacridones, diketopyrrolopyrrols, dioxazines, inanthrones, isoindolines, azo compounds, perylenes, phthalocyanines or pyranthrones. Further suitable pigments include effect pigments on a metal base or pearl gloss pigments on a metal oxide base.

Suitable chain extenders for the linear molecular weight structure of polycondensation polymers such as polyesters or polyamides are, for example, diepoxides, bis-oxazonlines, bis-oxazolones, bis-oxazines, diisocyanates, dianhydrides, bis-acyllactams, bis-maleimides, dicyanates, carbodiimides. Further suitable chain extenders include polymer compounds such as polystyrene polyacrylate polyglycidyl (meth)acrylate copolymers, polystyrene maleic acid anhydride copolymers, and polyethylene maleic acid anhydride copolymers.

Suitable optical brighteners are, for example, bis-benzoxazoles, phenylcuomarins, or bis(styryl)biphenyls and in particular optical brighteners of the formulas:

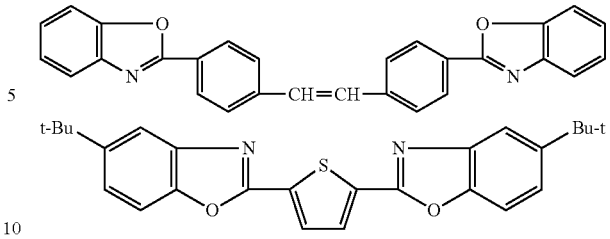

Suitable filler deactivators are, for example, epoxides such as bis-phenol-A-diglycidylethers, polysiloxanes, polyacrylates, in particular block copolymers such as polymethacrylic acid polyalkylene oxide.

Suitable antistatic agents are, for example, ethoxylated alkylamines, fatty acid esters, alkylsulfonates, and polymers such as polyetheramides.

Suitable antiozonants are the above-named amines such as N,N'-di-isopropyl-p-phenylene diamine, N,N'-di-sec-butyl-p-phenylene diamine, N,N'-bis(1,4-dimethylpentyl)-p-phenylene diamine, N,N'-dicyclohexyl-p-phenylene diamine, N-isopropyl-N'-phenyl-p-phenylene diamine, N-(1,3-dimethylbutyl)-N'-phenyl-p-phenylene diamine, N-(1-methylheptyl)-N'-phenyl-p-phenylene diamine, N-cyclohexyl-N'-phenyl-p-phenylene diamine.

Suitable demolding aids are, for example, montan waxes.

The following additives, selected from the group comprising phosphites, phosphonites, hydroxylamines, or nitrons, are very particularly preferably included in the composition in accordance with the invention.

In addition, the present invention relates to a method of stabilizing an organic component to be stabilized, in particular with respect to oxidative, thermal or actinic degradation or damage, in which at least one compound is mixed with the organic component to be stabilized or is worked into it.

Preferred embodiments of such a stabilization method provide, for example, that the compound in accordance with the invention can be present as a powder, as pellets, as a solution, as a liquid, as a suspension, as an emulsion, or as flakes and is transferred into the melt with the organic component to be stabilized, in particular the polymer or the plastic mixture to be stabilized, and is subsequently cooled. Alternatively to this, it is equally possible to introduce the compound in accordance with formula I into a polymer melt in a molten state.

For the case that further components are added to the polymer composition, they can be added to the polymers, as described above, separately, in the form of liquids, powders, dispersions, emulsions, pellets, or compacted products, or together with the additive composition in accordance with the invention.

The working in of the above-described compounds in accordance with the invention in accordance with formula I and, optionally, of the additional additives into the plastic takes place by conventional processing methods, wherein the polymer is melted and is mixed with the compounds in accordance with the invention in accordance with formula I and with the optional further additives, preferably by a mixer, a kneader, and an extruder. Extruders such as single-screw extruders, twin screw extruders, planetary gear extruders, ring extruders, and co-kneaders that are preferably equipped with a vacuum degassing are preferred as processing machines. The processing can here take place under air or optionally under inert gas conditions such as under nitrogen.

Furthermore, the compounds in accordance with the invention in accordance with formula I can be manufactured and introduced in the form of so-called master batches or concentrates that, for example, comprise 10- 90% of the compositions in accordance with the invention in a polymer.

In addition, the present invention relates to the use of the compounds in accordance with the invention in accordance with formula I for stabilizing organic materials against oxidative degradation or oxidative damage.

The present invention will be explained in more detail with reference to the following statements without restricting the invention hereto.

PREFERRED EMBODIMENTS

Method:

The conversion of an allyl compound or vinyl compound or Michael acceptor preferably takes place in a first reaction step with a thiol compound that additionally comprises an alcohol group with the aid of a catalyst and in a second reaction step the transesterification of the alcohol group takes place with an ester compound that comprises a sterically hindered phenol group. Mercaptoethanol, 3-mercaptopropanol, 2-mercaptopropanol, and 1-mercaptobutanol and thioglycerol are particularly preferred as the thiol compound. A further preferred method is the conversion of a thiopropyl compound that comprises a sterically hindered phenol group such as

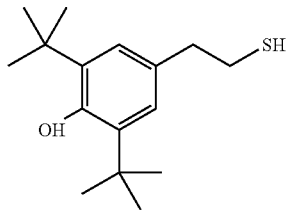 [SMILES: CC(C)(C)c1cc(CCS)cc(C(C)(C)C)c1O]

The reaction is preferably carried out in the presence of a catalyst; preferred catalysts are radical-generating compounds such as photoinitiators, azostarters, or peroxides and, for Michael acceptors, bases such as sodium methanolate, tritheylamine, or nucleophiles such as 1-methylimide azoles or alkylphosphines such as dimethylphenylphosphines.

The reaction can be carried out both in a substance and in a solvent; preferred solvents are inert solvents such as toluene, N-methyl-2-pyrrolidone or N,N-dimethylformamide. Methanol is furthermore used as the solvent. Particularly preferred reactions in the substance are preferably carried out in the surplus of the thiol component as a solvent/thinner.

The second reaction step, if necessary, preferably takes place by transesterification of the intermediately formed alcohol group with an ester that carries the sterically hindered phenol group. Corresponding methods and catalysts for transesterification are familiar to the skilled person and are described, for example, in J. Otera, Chem. Rev. 1993, 93, 1449-1470 (see enclosure) or also in WO 86/00301 (see enclosure) or WO2004/033699 (see enclosure). Metal compounds such as from the group of tin organyls or of titanates are preferred catalysts.

Use:

Plastics and oils and fats are preferred organic materials that can be stabilized by the stabilizers in accordance with the invention.

If the organic materials are oils and fats, they can be on the basis of mineral oils, vegetable fats, or animal fats, or also oils, fats, or waxes on the basis of e.g. synthetic esters.

Vegetable oils and fats are, for example, palm oil, olive oil, rape oil, linseed oil, soybean oil, sunflower oil, castor oil; animal fats are, for example, fish oils or suet.

The compounds in accordance with the invention can furthermore be used as stabilizers of lubricants, hydraulic oils, engine oils, turbine oils, transmission oils, metal machining fluids, or as lubricating greases. These mineral or synthetic lubricants are primarily based on hydrocarbons.

EMBODIMENTS

I. GENERAL SYNTHESIS RULE

The stabilizers in accordance with the invention are prepared in that first an allyl/vinyl compound is converted in a suitable reaction vessel using a stirring device at room temperature or at an elevated temperature with the thiol compound carrying the alcohol group in slight excess, preferably while adding a photocatalyst under UV lighting (Method A), a radical starter while heating (Method B), or, for electron withdrawing groups (EWGs), preferably while adding a base (Method C) in accordance with the following scheme:

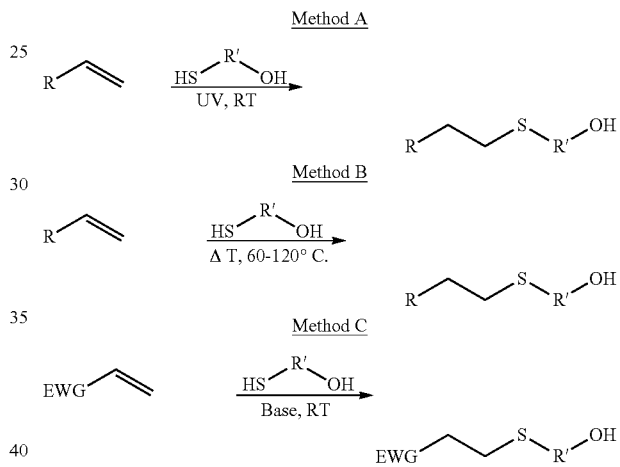

A destabilization or degassing of the reactants preferably takes place prior to the start of the reaction. The reaction and exposure times of Method A are 30 to 60 minutes. The reaction time for Method B is 4-35 h. A reaction under inert gas conditions is expedient for Method B. The reaction time of Method C amounts to a few minutes. The filtration takes place aqueously or via high vacuum at 60-100° C. In the second step, the transesterification takes place with the ester carrying a sterically hindered phenol group in slight excess at temperatures of 130-180° C. under metal catalysis in accordance with the scheme:

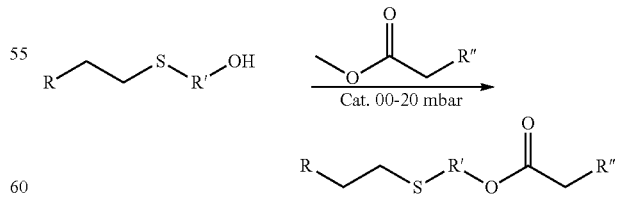

The alcohol produced is removed from the reaction mixture by applying a vacuum in the range 800-20 mbar. The filtration takes place under a high vacuum or aqueously. An addition of bleaching earth or of a different adsorption agent after intake into the solvent is expedient to adsorptively remove metallic catalyst residues.

II. SYNTHESIS OF EXAMPLES IN ACCORDANCE WITH THE INVENTION a) Synthesis of Example A in accordance with the invention:

In accordance with scheme 1

Scheme 1

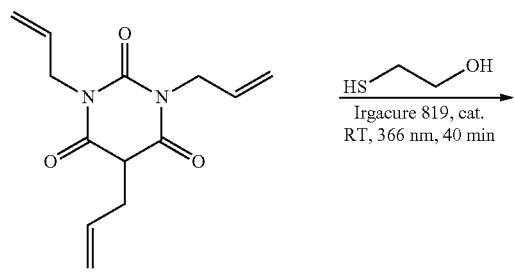

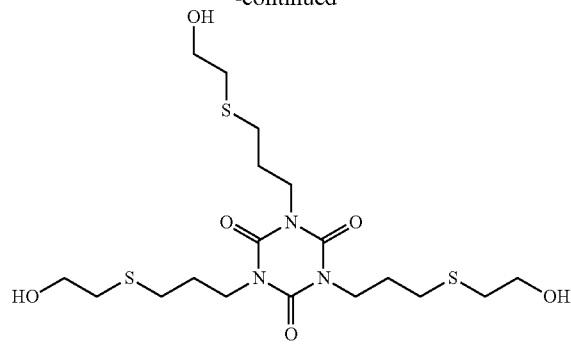

15.0 g (0.06 mol, 1 eq.) triallylisocyanurate are homogenized with 14.2 g (0.182 mol, 3.02 eq.) 2-mercaptoethanol in a round-necked flask using a magnetic stirrer at RT. 0.1 wt % phenyl-bis(2,4,-6-trimethylbenzoyl)-phosphinoxide (photoinitiator, with respect to the isocyanurate) are added to the mixture and stirring takes place under UV lighting at $\lambda$=366 nm and RT for 30-40 min. The reaction monitoring takes place via $^1$H NMR analysis. The transparent, low-viscosity solution is received in 150 ml ethyl acetate and is washed twice with 50 ml distilled water in each case, the organic phase is separated, and the solvent is removed under high vacuum at 60° C. 27.6 g (95%) of a transparent, high-viscosity gel are obtained.

In accordance with scheme 2

Scheme 2

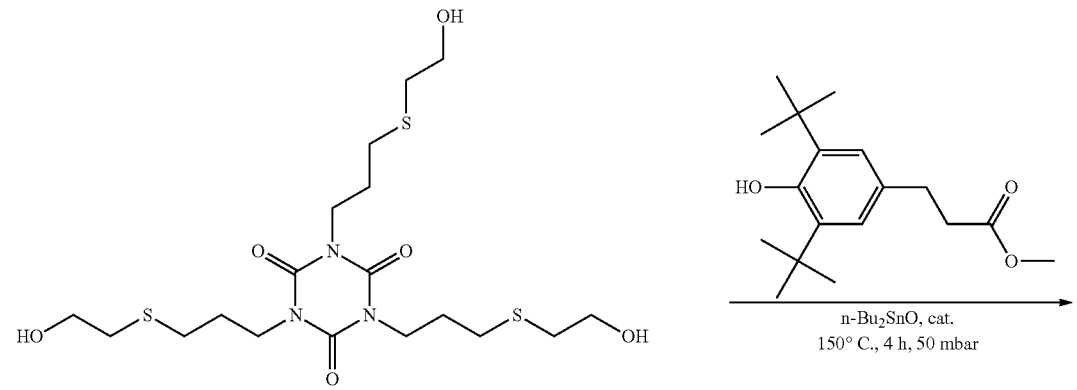

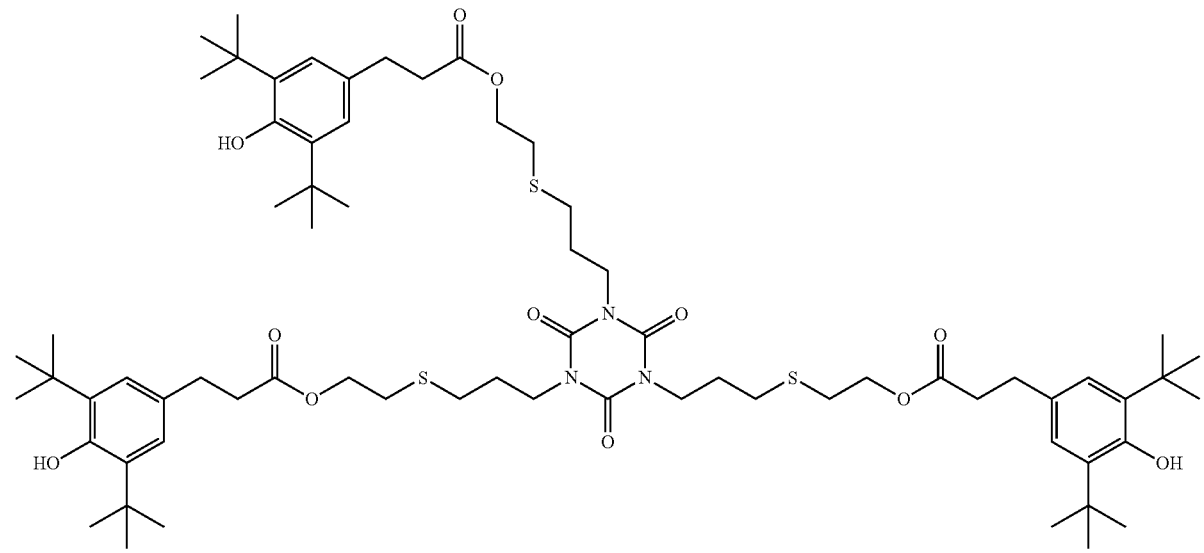

10 g (0.021 mol, 1 eq.) of the thioether are melted at 80° C. under nitrogen with 18.26 g (0.62 mol, 3.02 eq.) 3-(3,5-di-tert. butyl-4-hydroxyphenyl)propionic acid methyl ester in a Schlenk flask using a magnetic stirrer, a condensation bridge, and a cold trap. 0.15 mol % n-Bu$_2$SnO (with respect to the thioether) is added to the clear melt, the reaction mixture is heated up to 150° C. and is stirred for ~4 h at ~50 mbar. The reaction monitoring takes place via $^1$H NMR analysis. After conversion has taken place, the vacuum is increased to <5 mbar and the remaining 3-(3,5-di-tert. butyl-4-hydroxyphenyl)propionic acid methyl ester is condensed off. The vacuum is canceled with N$_2$ and the reaction mixture is cooled to RT, with the melt solidifying to a hard, glass-like mass. The transesterification product is received in toluene and is subsequently washed twice with 50 mol conc. NaHCO$_3$ solution and subsequently twice with distilled water up to pH neutrality. The organic phase is dried over Na$_2$SO4, is filtered via a glass filter funnel, and the solvent is removed under vacuum. A hard, glass-like solidified solid of 19.6 g (75%) remains. The structure was confirmed by its $^1$H NMR spectrum.

$^1$H NMR (300 MHz, CDCl$_3$) δ=6.91 (s, 6H, —C$_{arom.}$—H), 5.00 (s, 3H, —C$_{arom.}$—OH), 4.15 (t, 6H, —COOCH$_2$—), 3.92 (t, 6H, —N—CH$_2$—), 2.79 (t, 6H, —C$_{arom.}$—CH$_2$-), 2.65 (t, 6H, —S—CH$_2$—CH$_2$O—), 2.59-2.44 (m, 12H, —N—(CH$_2$)$_2$—CH$_2$—, O=C—CH$_2$-), 1.87 (p, 6H, —N—CH$_2$—CH$_2$—CH$_2$—), 1.35 (s, 54H, —CH$_3$).

$^{13}$C NMR (76 MHz, CDCl$_3$) δ=173.08, 152.31, 149.09, 136.08, 131.10, 124.91, 63.41, 42.32, 36.50, 34.45, 31.08, 30.47, 29.64, 27.61.

In accordance with scheme 3

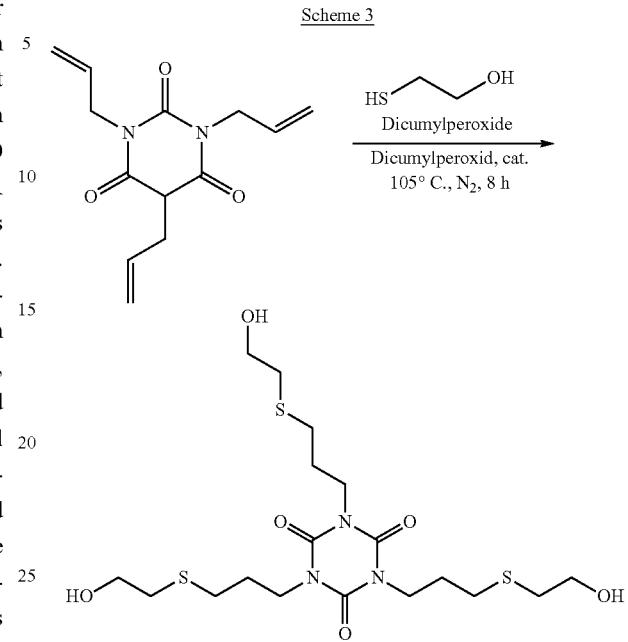

Scheme 3

5.20 g (20.86 mmol, 1 eq.) triallylisocyanurate are dissolved and homogenized with 11.08 g (141.85 mmol, 6.8 eq.) 2-mercaptoethanol in a 50 m Schlenk flask with septum while stirring. The clear solution is degassed with N2 for 1 h. The septum is replaced with a reflux condenser having a bubble counter under N2 and the solution is heated to 105° C. Once the temperature has been reached, 16 mg dicumyl peroxide is added and the reaction mixture is stirred at 105° C. for 8 h. The reaction monitoring takes place via $^1$H NMR analysis by reduction of the C=C double bonds. The clear solution is liberated of excess thiol and is filtered under vacuum (10$^{-2}$ mbar) at 80° C. A transparent gel of 9.97 g (97% of the theoretical value)

In accordance with scheme 4

Scheme 4

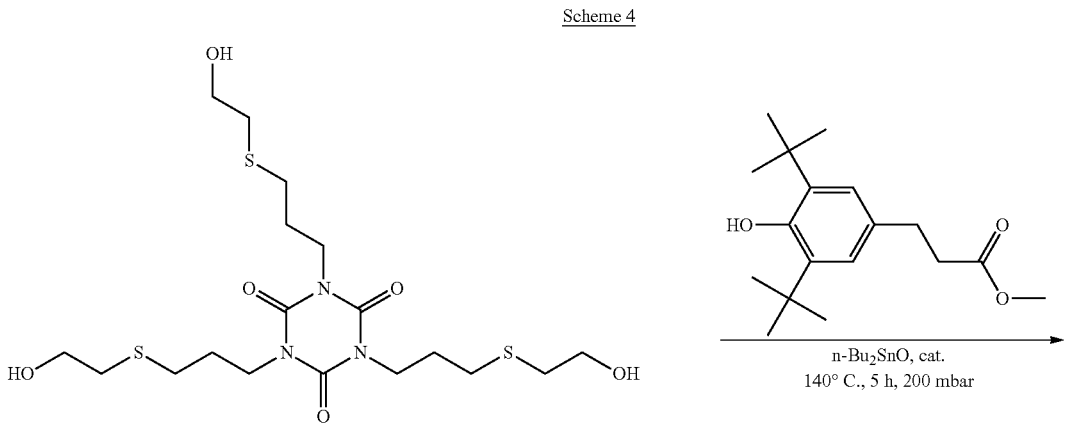

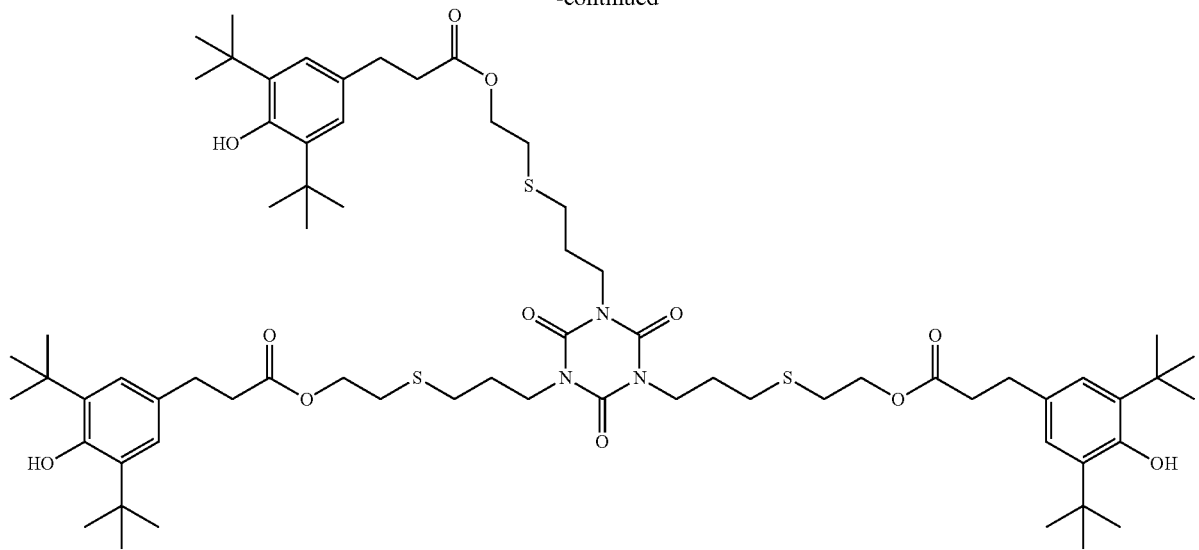

7.65 g (15.82 mmol, 1 eq.) of the thioether precursor are melted and homogenized at 80° C. under $N_2$ with 15.51 g (53.04 mol, 3.35 eq.) 3-(3,5-di-tert. butyl -4-hydroxyphenyl) propionic acid methyl ester (Metilox) in a 100 ml Schlenk flask using a condensation bridge and a cold trap with a vacuum connection. 156.83 mg (4.98 mmol, 0.31 eq.) DBTO are added to the clear melt under $N_2$ and the temperature is elevated to 140° C. A slight vacuum of ~200 mbar is applied and the reaction mixture is stirred for 5 h. After the end of the reaction period, the pressure is reduced to $10^{-3}$ mbar, the temperature is elevated to 160° C., and excess Metilox is condensed off. After gassing with $N_2$, the transparent reaction melt is cooled to RT and is subsequently received in dichloromethane. 1.4 g acid activated bleaching earth (Optimum 210 FF, Clariant) is added while stirring and the suspension is refluxed for 30 min. Filtration takes place via a short silica pad and the solvent is removed under vacuum. A glass-like transparent solid of 16.86 g (83% of the theoretical value) remains. The structure was confirmed by its 1H NMR spectrum.

$^1$H NMR (300 MHz, Chloroform-d) δ=6.91 (s, 6H, -Carom.—OH), 5.00 (s, 3H, -$C_{arom.}$—OH), 4.15 (t, 6H, —$COOCH2$—), 3.92 (t, 6H, —N—C$\underline{H}H_2$—), 2.79 (t, 6H, —$C_{arom.}$—C$\underline{H}_2$—), 2.65 (t, 6H, —S—$CH_2$—$CH_2O$—), 2.60-2.37 (m, 12H, —N($CH_2$)$_2$—$CH_2$—, O=C—$CH_2$—), 1.87 (p, 6H, —N—$CH_2$—$CH_2$—$CH_2$—), 1.35 (s, 54H, —C$\underline{H}_3$).

$^{13}$C NMR (76 MHz, Chloroform-d) δ=172.98, 152.20, 148.98, 135.97, 130.99, 124.80, 63.29, 42.20, 36.38, 34.33, 30.95, 30.34, 29.52, 27.49 ppm.

b) Synthesis of Example B in accordance with the invention:

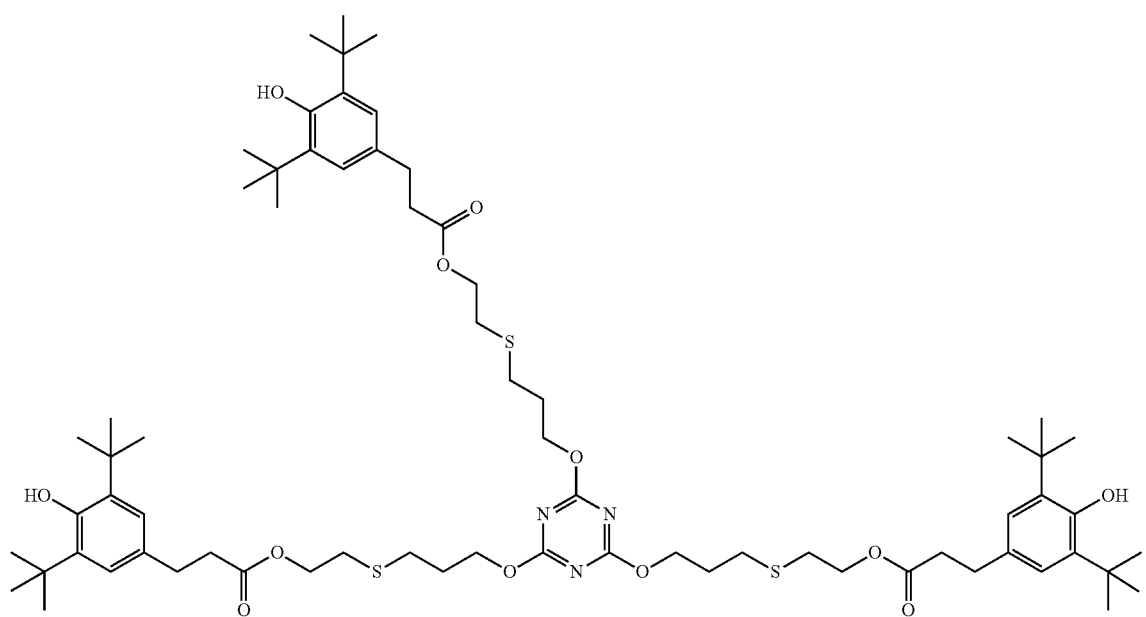

FIG. 1

Analog to Example A scheme 1, 5.00 g (0.020 mol, 1 eq.) triallylcyanurate are converted with 4.78 g (0.061 mol, 3.05 eq.) 2-mercaptoethanol at an exposure time of 50 min. Filtering takes place under a high vacuum at 60° C. 9.1 g (94% of the theoretical value) of a transparent, pale yellow, and medium viscosity gel are obtained.

Analog to Example A scheme 2, 4 g (0.080 mol, 1 eq.) of the thioether are converted and finished aqueously with 7.74 g (0.02g mol, 3.25 eq.) 3-(3,5 di-tert-butyl-4-hydroxyphenyl) propionic acid methyl ester at 100 mbar. A hard, yellowish transparent solid remains. The yield is 9.20 g (88% of the theoretical value). The structure in accordance with FIG. 1 was confirmed by its $^1$H NMR spectrum.

$^1$H NMR (300 MHz, CDCl$_3$) δ=6.91 (s, 6H, —C$_{arom.}$—HH), 5.00 (s, 3H, —C$_{arom.}$—OH), 4.14 (t, 6H, —COOCH$_2$—), 3.91 (t, 6H, —OCH$_2$—), 2.79 (t, 6H, —C$_{arom.}$—CH$_2$-), 2.65 (t, 6H, —S—CH$_2$—CH$_2$O—), 2.58-2.47 (m, 12H, —S—CH$_2$—(CH$_2$)$_2$O—, O=C—CH$_2$—), 1.87 (p, 6H, —O—CH$_2$—CH$_2$—CH$_2$—), 1.35 (s, 54H, —CH$_3$).

$^{13}$C NMR (76 MHz, CDCl$_3$) δ172.97, 152.20, 135.97, 130.99, 124.80, 63.30, 42.21, 36.39, 34.34, 30.97, 30.36, 29.52, 27.50.

Analog to Example A scheme 3, 5.21 g (20.90 mmol, 1 eq.) triallylcyanurate are converted with 7.97 g (102.01 mmol, 4.88 eq.) 2-mercaptoethanol at 110° C. within a reaction time of 31 h. Filtration takes place under a high vacuum at 100° C. A transparent gel of 9.01 g (89% of the theoretical value) remains.

Analog to Example A scheme 4, 9.00 g (18.61 mmol, 1 eq.) of the thioether are converted with 22.40 g (76.60 mmol, 4.12 eq.) 3-(3,5-di-tert. butyl-4-hydroxyphenyl)propionic acid methylester at 50-200 mbar and are filtered, as described, with 2.8 g bleaching earth. The yield of the glass-like transparent and high viscosity resin amounts to 14.27 g (61% of the theoretical value). The structure in accordance with FIG. 1 was confirmed by its $^1$H NMR spectrum.

$^1$H NMR (300 MHz, Chloroform-d) δ=6.91 (s, 6H, —C$_{arom.}$—HH), 5.00 (s, 3H, —C$_{arom.}$—OH), 4.40 (t,6H, —C$_{arom.}$—O—CH$_2$—), 4.16 (t, 6H, —COOCH$_2$—), 2.79 (t, 6H-C$_{arom.}$—CH$_2$—), 2.65 (td, 12H, —CH$_2$—S—CH$_2$—), 2.57-2.50 (m, 6H, O=C—CH$_2$—), 1.99 (p, 6H, —O—CH$_2$—CH$_2$—CH$_2$—), 1.35 (s, 54H, —CH$_3$) ppm.

$^{13}$C NMR (76 MHz, Chloroform-d) δ=173.01, 172.98, 152.20, 135.97, 130.98, 124.80, 66.73, 63.33, 36.37, 34.33, 30.96, 30.50, 30.34, 28.64 ppm.

c) Synthesis of Example C in accordance with the invention:

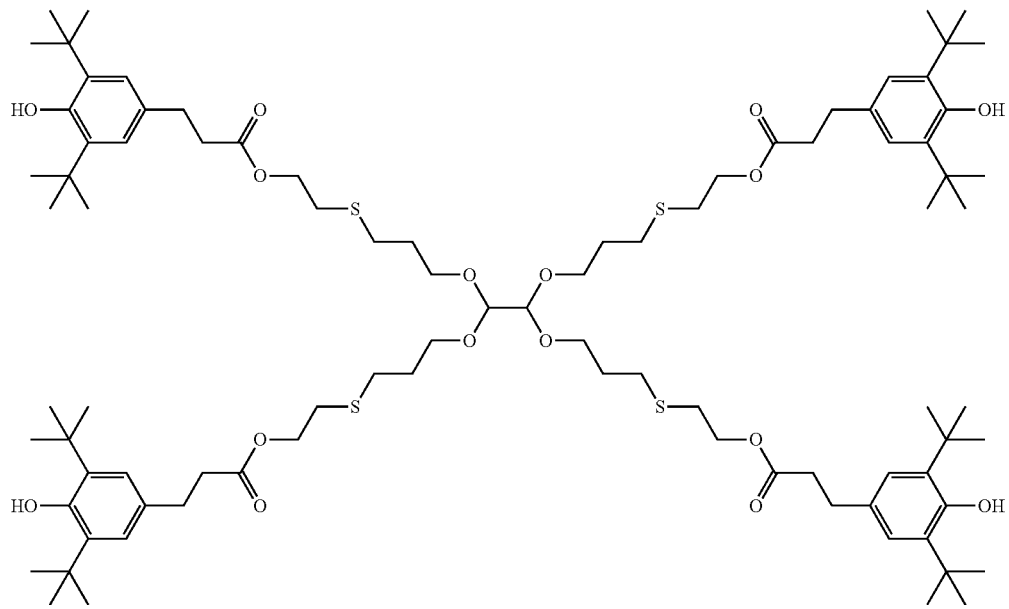

FIG.2

Analog to Example A scheme 1, 7.0 g (0.028 mol, 1 eq.) tetraallyloxyethane are converted with 8.8 g (0.113 mol, 4.1 eq.) 2-mercaptoethanol. The exposure time is 60 min. After an aqueous finishing analog to Example A, filtering continues under high vacuum at 80° C. and solvent is removed. 13.6 g (87% of the theoretical value) of a transparent, amber gel of low viscosity are obtained.

Analog to Example A scheme 2, 3.52 g (0.006 mol, 1 eq.) of the thioether are converted with 7.72 g (0.025 mol, 4.0 eq.) 3-(3,5-di-tert. - butyl-4-hydroxyphenyl)propionic acid methyl ester at 140° C. and ~80 mbar. The raw product is dissolved in approximately 200 ml ethyl acetate and is aqueously finished analog to Example A. 9.25 g (92% of the theoretical value) of a transparent, amber gel of high viscosity are obtained. The structure in accordance with FIG. 2 was confirmed by its $^1$H NMR spectrum.

$^1$H NMR (300 MHz, CDCl$_3$) δ=6.91 (s, 8H, —C$_{arom.}$—H), 5.00 (s, 4H, —C$_{arom.}$—OH), 4.25 (s, 2H,—CH—CH—), 4.15 (t, 8H, —COOCH$_2$—), 3.76-3.46 (m, 8H, —CH—O—HH$_2$), 2.79 (t, 8H, —C$_{arom.}$—CH$_2$—), 2.64 (t, 8H, O=C—CH$_2$—)2.70-2.42 (m, 16H, —CH$_2$—S—CH$_2$—), 1.79 (p, 8H, —S—CH$_2$—CH$_2$—CH$_2$—O—), 1.35 (s,72H, —CH$_3$).

$^{13}$C NMR (76 MHz, CDCl$_3$) δ172.97, 152.19, 135.94, 130.99, 124.79, 102.37, 66.01, 63.36, 36.38, 34.33, 30.96, 30.34, 29.84, 28.92.

Analog to Example A scheme 3, 5.00 g (19.66 mmol, 1 eq.) tetraallyloxyethane are stirred with 7.37 g (94.33 mmol, 4.8 eq.) 2-mercaptoethanol and 216 mg (0.80 mmol, 0.04 eq.) dicumyl peroxide at 100° for 2 h. 1.34 g (17.15 mmol, 1.15 eq.) 2-mercaptoethanol are again added and are stirred for a further 2.5 h. Filtration takes place under a high vacuum at 100° C. A transparent, light yellow gel of 10.07 g (90% of the theoretical value) remains.

Analog to Example A scheme 4, 8.59 g (15.15 mmol, 1 eq.) of the thioether are converted with 19.50 g 66.68 mmol, 4.12 eq.) 3-(3,5-di-tert. butyl-4-hydroxyphenyl)propionic acid methylester at 50-200 mbar and are filtered, as described, with 2.8 g bleaching earth. The yield of the glass-like, transparent, and light yellow, high viscosity resin amounts to 14.27 g (61% of the theoretical value). The structure in accordance with FIG. 2 was confirmed by its $^1$H NMR spectrum.

$^1$H NMR (300 MHz, Chloroform-d) δ=6.91 (s, 8H, —C$_{arom.}$—H), 5.00 (s, 4H, —C$_{arom.}$—OH), 4.25 (s, 2H,—CH—CH—), 4.15 (t, 8H, —COOCH$_2$—), 3.75-3.43 (m, 8H, —CH—O—CH$_2$), 2.80 (t, 8H, —C$_{arom.}$—CH$_2$—), 2.64 (t, 8H, O=C—CH$_2$—), 2.61-2.48 (m, 16H, —CH$_2$—S—CH$_2$—), 1.79 (p, 8H, —S—CH$_2$—CH$_2$—CH$_2$—O—), 1.35 (s, 72H, —CH$_3$) ppm.

$^{13}$C NMR (76 MHz, chloroform-d) δ=172.97, 152.20, 135.95, 131.00, 124.80, 102.38, 66.02, 63.36, 36.38, 34.33, 30.96, 30.35, 29.85, 28.92.

Analog to Example A scheme 2, 4.12 g (0.023 mol, 1 eq.) of the thioether are converted with 7.72 g (0.025 mol, 1.1 eq.) 3-(3,5-di-tert. - butyl-4-hydroxyphenyl)propionic acid methyl ester at 140° C. and ~800 mbar. The raw product is received in approximately 150 ml toluene and is aqueously finished analog to Example A. 9.27 g (93% of the theoretical value) of a transparent, yellowish gel of high viscosity are obtained. The structure in accordance with FIG. 3 was confirmed by its $^1$H NMR spectrum.

$^1$H NMR (300 MHz, CDCl$_3$) δ=7.29-7.05 (m, 5H, —C$_{arom., Styrol}$—H), 6.91 (s, 2H, —C$_{arom., Metilox}$—H), 4.99 (s, 1H, —C$_{arom., Metilox}$—OH), 4.15 (t, 2H, COOCH$_2$—), 2.86-2.68 (m, 6H, —CH$_2$—S—CH$_2$—CH$_2$—), 2.65 (t, 2H, C$_{arom., Metilox}$—CH$_2$), 2.59-2.46 (m, 2H, O=C—CH$_2$—), 1.35 (s, 18H, —CH$_3$).

$^{13}$C NMR (76 MHz, CDCl$_3$) δ=140.23, 128.63, 128.54, 128.50, 128.35, 126.49, 125.85, 60.30, 36.37, 35.50, 33.22.

e) Synthesis of Example E in accordance with the invention:

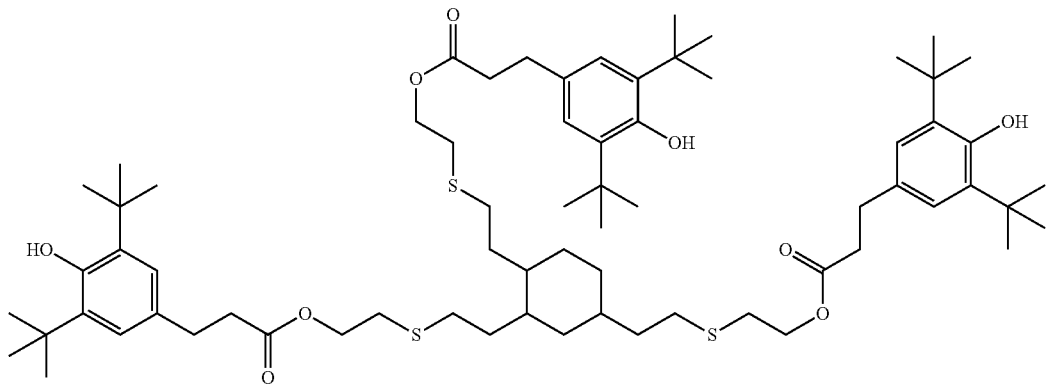

FIG. 4 d) Synthesis of Example D in accordance with the invention:

FIG. 3

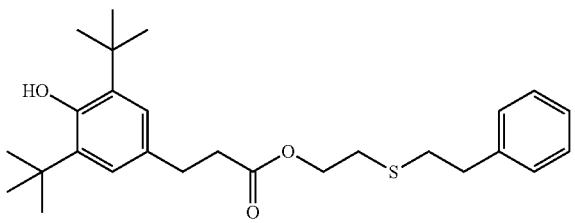

Analog to Example A scheme 1, 5.71 g (0.055 mol, 1 eq.) styrene are converted with 4.71 g (0.060 mol, 1.1 eq.) mercaptoethanol and 0.2 wt. % phenyl-bis(2,4,6-trimethyl-benzoyl)-phosphine oxide (photoinitiator, with respect to the styrene). The transparent, low viscosity raw product is received in approximately 100 ml dichloromethane and is aqueously finished analog to Example A. 7.48 g (75% of the theoretical value) of a transparent, gel of low viscosity are obtained.

Analog to example A scheme 1, werden 6.00 g (0.037 mol, 1 eq.) trivinylcyclohexane are converted with 8.81 g (0.113 mol, 3.05 eq.) 2-mercaptoethanol with 0.2 wt % phenyl-bis(2,4,6-trimethylbenzoyl)-phosphine oxide (photoinitiator, with respect to the trivinylcyclohexane). The transparent, medium viscosity and pale yellow raw product is received in approximately 100 ml diethylether and is aqueously finished analog to Example A. After further filtering under a high vacuum at 80° C., 13.8 g (94% of the theoretical value) of a transparent, pale yellow, and medium viscosity gel are obtained.

Analog to Example A Scheme 2, 4.00 g (0.010 mol, 1 eq.) of the thioether are converted with 8.99 g (0.031 mol, 3:05 eq.) 3-(3,5-di-tert. - butyl-4-hydroxyphenyl)propionic acid methyl ester at 150° C. and ~100 mbar. The filtration takes place aqueously analog to Example A. A tough, yellowish transparent resin remains with a yield of 10.21 g (86% of the theoretical value). The structure in accordance with FIG. 4 was confirmed by its $^1$H NMR spectrum.

$^1$H NMR (300 MHz, CDCl$_3$) δ=6.91 (s, 6H, C$_{arom.}$—H), 5.00 (s, 3H, —C$_{arom.}$—OH), 4.15 (t, 6H, —COOCH$_2$—), 2.90-2.73 (t, 6H, —C$_{arom.}$—CH$_2$), 2.64 (t, 6H, O=C-CH$_2$), 2.60-2.31 (m, 12H, —CH$_2$—S—CH$_2$—), 1.35 (s, 54H, -CH$_3$), 1.99-0.38 (m, 15H, —CH$_2$—CH$_{Ring, aliph.}$, C $\underline{H}_{2,Ring,aliph.}$). $^{13}$C NMR (76 MHz, CDCl$_3$) δ=173.00, 152.20, 135.97, 131.01, 124.81, 63.45, 40.71, 38.44, 37.07, 36.61, 36.42, 34.35, 33.28, 32.39, 31.00, 30.61, 30.38, 29.91, 29.54.

f) Synthesis of Example F in accordance with the invention:

FIG. 5

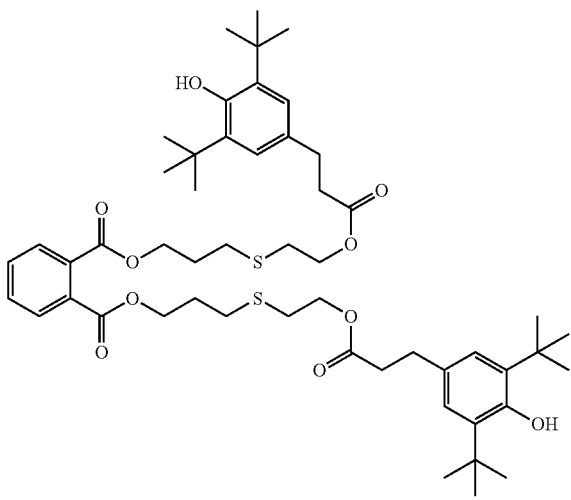

Analog to Example A Scheme 1, 6.12 g (0.025 mol, 1 eq.) diallylphthalate are converted with 4.08 g (0.052 mol, 2.1 eq.) 2-mercaptoethanol and 0. 2 wt % phenyl-bis(2,4,6-trimethylbenzoyl)-phosphine oxide (photoinitiator, with respect to the diallylphthalate). Filtering takes place under a high vacuum at 60° C. 9.91 g (99% of the theoretical value) of a transparent, pale yellow, and low viscosity gel are obtained.

Analog to Example A Scheme 2, 3.50 g (0.009 mol, 1 eq.) of the thioether are converted with 5.09 g (0.174 mol, 2.0 eq.) 3-(3,5-di-tert. - butyl-4-hydroxyphenyl)propionic acid methyl ester at 140° C. and ~800 mbar. Filtering takes place under a high vacuum at 140° C. 7.38 g (74% of the theoretical value) of a transparent, pale yellow, and low viscosity gel are obtained. The structure in accordance with FIG. 5 was confirmed by its $^1$H NMR spectrum.

$^1$H NMR (300 MHz, CDCl$_3$) δ=7.64 (m, 2H,—C—C$_{arom., Phthalat}$—$\underline{H}$), 7.55-7.37 (m, 2H, —C$_{arom., Phthalat}$—$\underline{H}$), 6.91 (s, 4H, —C$_{arom., Metilox}$—$\underline{H}$), 5.00 (s, 2H, —C$_{arom.}$—O$\underline{H}$), 4.44-4.28 (m, 4H, —C$_{arom., Phthalat}$—COOC$\underline{H}_2$), 4.22-4.04 (m, 4H, —CH$_2$COOC$\underline{H}_2$—), 2.79 (t, 6H, —C$_{arom.}$—C$\underline{H}_2$—), 2.70-2.48 (m, 12H), 1.96 (p, 4H, —S—CH$_2$—C$\underline{H}_2$—CH$_2$—), 1.35 (s, 36H, —C$\underline{H}_3$).

$^{13}$C NMR (76 MHz, CDCl$_3$) δ=172.97 , 167.40 , 152.19 , 135.95 , 131.99 , 131.14 , 130.97 , 128.91, 124.79 , 64.12 , 63.33 , 62.83 , 36.37 , 34.32 , 30.95 , 30.48 , 30.34 , 28.74 , 28.67.

Analog to Example A Scheme 3, 9.18 g (37.28 mmol, 1 eq.) diallylphthalate are stirred with 6.99 g (89.47 mmol, 2.4 eq.) 2-mercaptoethanol and 180 mg (1.1 mmol, 0.02 eq.) azobis(2-methylpropionitrile) at a reaction temperature of 70° C. for 1 h. 0.04 g (0.24 mmol, 0.006 eq.) 2-2'-azobis(2-methylpropionitrile) are again added and are mixed at 80° C. for a further 9 h. Filtration takes place under a high vacuum at 80° C. A transparent , light yellow, low viscosity gel of 13.68 g (91% of the theoretical value) remains.

Analog to Example A Scheme 4, 8.72 g (21.66 mmol, 1 eq.) of the thioether are converted with 12.99 g (44.42 mmol, 2.05 eq.) 3-(3,5-di-tert. butyl-4-hydroxyphenyl)propionic acid methylester at 50-200 mbar and are filtered, as described, with 1.4 g bleaching earth. The yield of the transparent and light yellow, high viscosity resin amounts to 8.77 g (87% of the theoretical value). The structure in accordance with FIG. 5 was confirmed by its $^1$H NMR spectrum.

$^1$H NMR (300 MHz, Chloroform-d) δ=7.72-7.60 (m, 2H, —C—C$_{arom., Phthalat}$—$\underline{H}$), 7.53-7.39 (m, 2H, —C$_{arom., Phthalat}$—$\underline{H}$), 6.92 (s, 4H, —C$_{arom., Metilox}$—$\underline{H}$), 5.00 (s, 2H, —C$_{arom.}$—O$\underline{H}$), 4.35 (t, 4H, —C$_{arom., Phthalat}$—COOC$\underline{H}_2$—), 3.66 (t, 4H, —CH$_2$COOC$\underline{H}_2$—), 2.80 (t, 4H, C$_{arom.}$—C$\underline{H}_2$—), 2.64-2.49 (m, 8H, —C$\underline{H}_2$—S—C$\underline{H}_2$), 1.97 (p, 4H, —S—CH$_2$—C$\underline{H}_2$—CH$_2$—), 1.36 (s, 36H, —C$\underline{H}_3$).

g) Synthesis of Example G in accordance with the invention:

In accordance with Scheme 5

Scheme 5

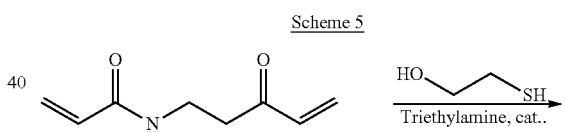

5.40 g (35.03 mmol, 1 eq.) N,N'-methylene-bis-acrylamide are stirred and suspended with 12.21 g (156.28 mmol, 4.5 eq.) 2-mercaptoethanol and 370 mg (3.6 mmol, 0.1 eq.) in 20 ml methanol The suspension clarifies homogeneously and transparently when heated, with a white solid being precipitated after a few minutes. The solid is filtered off, is washed three times with 15 ml distilled water and 15 ml methanol, and is dried in the drying cabinet. A white solid of 7.40g (68% of the theoretical value) remains.

FIG. 6

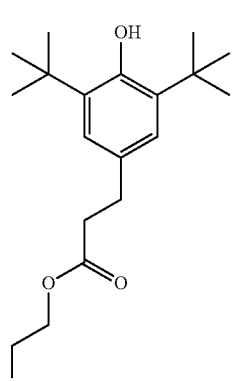
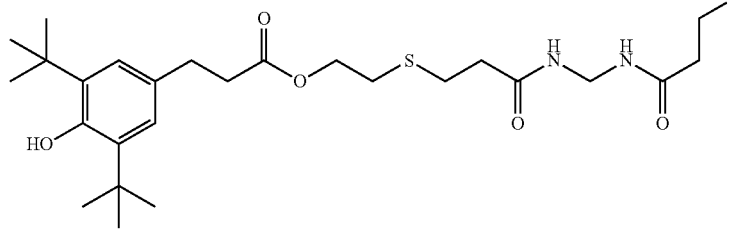

Analog to Example A Scheme 4, 6.95 g (22.38 mol, 1 eq.) of the thioether are converted with 31.30 g (107.04 mol, 4.8 eq.) 3-(3,5-di-tert. - butyl-4-hydroxyphenyl)propionic acid methyl ester at 160° C. and 50- 200 mbar within 8 h. The filtration takes place as described with 1.4 g bleaching earth. 16.72 g (90% of the theoretical value) of a glass-like, light brown solid are obtained. The structure in accordance with FIG. 6 was confirmed by its $^1$H NMR spectrum.

$^1$H NMR (300 MHz, Chloroform-d) δ=6.91 (s, 4H, —C$_{arom.}$—H), 6.87 (t, 2H, —NH—CH$_2$—NH—), 5.02 (s, 2H, —C$_{arom.}$—OH), 4.54 (t, 2H, —NH—CH$_2$—NH—), 4.15 (t, 4H, —C$_{arom.}$—COOCH$_2$—), 2.86-2.73 (m, 8H, —NH—CO—CH$_2$—, —C$_{arom.}$—CH$_2$—CH$_2$—), 2.54 (t, 4H, —C$_{arom.}$—CH$_2$) 2.39 (t, 4H, C$_{arom.}$—CH$_2$—), 1.35 (s, 36H, -CH$_3$).

$^{13}$C NMR (76 MHz, Chloroform-d) δ=173.06, 172.06, 152.21, 136.01, 130.96, 124.80, 63.37, 44.67, 36.42, 36.37, 34.33, 30.94, 30.74, 30.35, 27.67 ppm.

h) Synthesis of Example H in accordance with the invention:

Analog to Example A Scheme 2, 3.25 g (6.99 mol, 2.1 eq.) of the thioether are converted with 4.29 g (14.69 mol, 2.1 eq.) 3-(3,5-di-tert. - butyl-4-hydroxyphenyl)propionic acid methyl ester at 145° C. and 50- 200 mbar within 5 h. Filtering takes place under a high vacuum at 150° C. 6.07 g (88% of the theoretical value) of a transparent, yellowish, and high viscosity resin are obtained. The structure in accordance with FIG. 7 was confirmed by its $^1$H NMR spectrum.

$^1$H NMR (300 MHz, Chloroform-d) δ=6.91 (s, 4H, —C$_{arom.}$—CH), 6.87-6.70 (m, 4H, —CH$_2$-C$_{Bisphenol}$—CH$_2$), 6.57 (s, 2H, —C$_{Bisphenol}$OH—CH$_2$), 5.15 (s, 2H, —C$_{Bisphenol}$—OH), 5.00 (s, 2H, —C$_{arom.}$—OH), 4.14 (t, 4H, —COO—CH$_2$—CH$_2$—S—), 2.80 (t, 4H,

FIG. 7

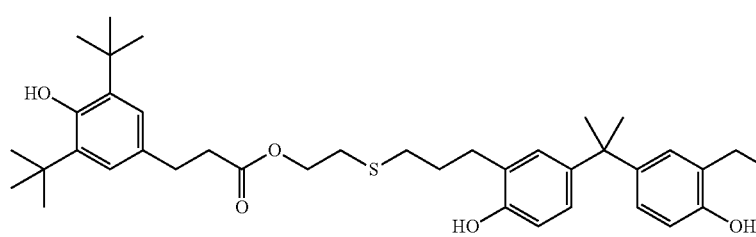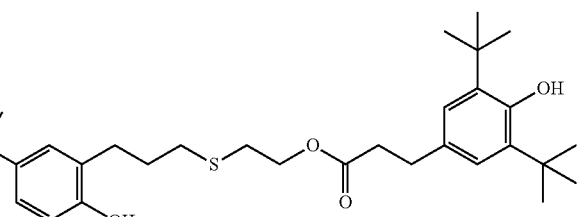

Analog to Example A Scheme 1, 6.64 g (21.53 mol, 1 eq.) o,o' diallylbisphenol A are converted with 3.45 g (44.16 mol, 2:05 eq.) 2-mercaptoethanol with 0.1 wt % phenyl-bis(2,4, 6-trimethylbenzoyl)-phosphine oxide (photoinitiator, with respect to the diallyl). Filtering takes place under a high vacuum at 60° C. 9.04 g (90% of the theoretical value) of a transparent, yellowish, and low viscosity gel are obtained.

—C$_{arom.}$—CH$_2$—CH$_2$—COO—), 2.68-2.50 (m, 12H), 2.46 (t, 4H, —C$_{arom.}$—CH$_2$—CH$_2$—COO—), 1.80 (p, 4H, —S—CH$_2$—CH$_2$—CH$_2$—), 1.52 (s, 6H, —C$_{Bisphenol}$H$_3$), 1.35 (s, 36H, —CH$_3$).

$^{13}$C NMR (76 MHz, Chloroform-d) δ=173.29, 152.22, 151.57, 143.31, 135.98, 130.97, 128.84, 126.45, 125.64, 114.97, 63.53, 41.66, 36.40, 34.33, 31.69, 30.95, 28.93.

i) Synthesis of Example I in accordance with the invention:

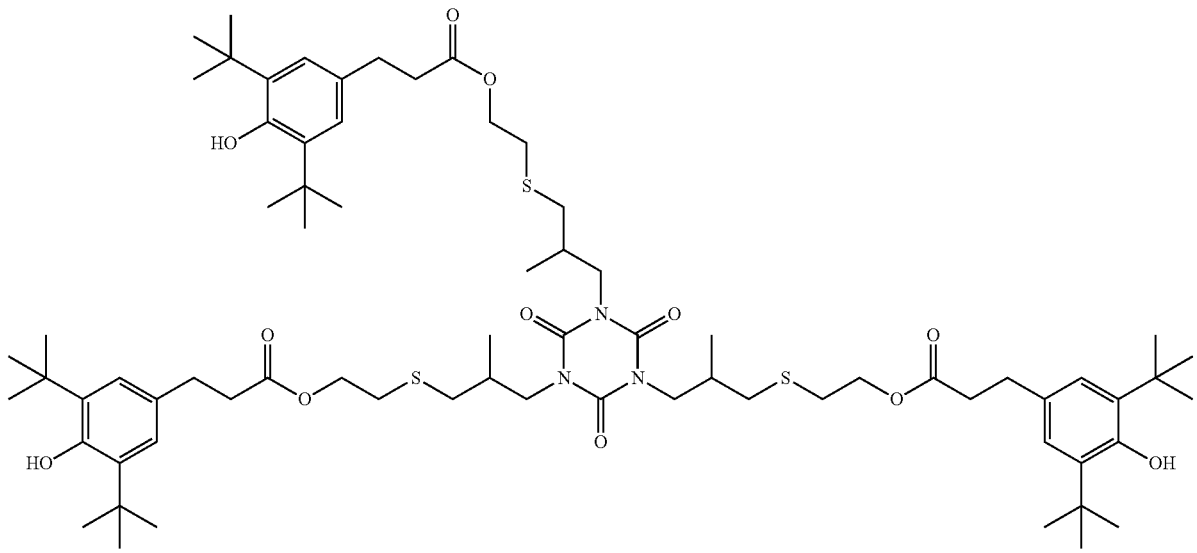

FIG. 8

Analog to Example A Scheme 3, 5.56 g (19.08 mmol, 1 eq.) trimethylallylisocyanurate are stirred with 9.63 g (123.26 mmol, 6.46 eq.) 2-mercaptoethanol and 160 mg (0.60 mmol, 0.03 eq.) dicumyl peroxide at a reaction temperature of 115° C. for 8 h. Filtration takes place under a high vacuum at 80° C. A transparent , light yellow gel of 7.14 g (71% of the theoretical value) remains.

Analog to Example A Scheme 4, 7.00 g (13.31 mmol, 1 eq.) of the thioether are converted with 16.24 g (55.54 mmol, 4.12 eq.) 3-(3,5-di-tert. butyl-4-hydroxyphenyl)propionic acid methyl ester at 50-200 mbar and are filtered, as described, with 2.8 g bleaching earth. The yield of the glass-like, transparent, and light orange, glass-like resin amounts to 16.29 g (94% of the theoretical value). The structure in accordance with FIG. 8 was confirmed by its $^1$H NMR spectrum.

$^1$H NMR (300 MHz, Chloroform-d) δ=6.91 (s, 6H, —$C_{arom.}$—C$\underline{H}$), 5.00 (s, 3H, —$C_{arom.}$—O$\underline{H}$), 4.12 (t, 6H, —COO—C$\underline{H}_2$—CH$_2$—S—), 3.89 (dd, 3H, —N—CH$_2$'), 3.73 (dd, 3H, —N—CH$_2$"—), 2.79 (t, 6H, —$C_{arom.}$—C$\underline{H}_2$—), 2.63 (t, 6H, ⇒COO—CH$_2$—C$\underline{H}_2$—S—), 2.53 (m, 9H, —$C_{arom.}$—CH$_2$—CH$_2$—, —S—C$\underline{H}_2$'—CH—), 2.41 (dd, 3H, —S—C$\underline{H}_{2"-CH-}$), 2.18 (p, 3H, —N—CH$_2$—C$\underline{H}$—), 1.35 (s, 54H, —C$\underline{H}_3$), 0.95 (d, 9H, —CH—C$\underline{H}_3$).

j) Synthesis of polymer Example J in accordance with the invention:

20.88 g (83.76 mmol, 1 eq.) triallylisocyanurate are dissolved in 6.66 g (85.24 mmol, 0.98 eq.)2-mercaptoethanol in a heated 100 mL Schlenk flask. The reaction mixture is degassed twice using the freeze-pump-thaw method. After the addition of a spatula tipopf phenyl-bis(2,4,6-trimethylbenzoyl)-phosphine oxide (photoinitiator), the reaction mixture is irradiated with UV light of the wavelength 366 nm for 1 h. In this process, a clear increase of the viscosity of the reaction mixture can be observed after half an hour. The reaction mixture is subsequently heated to 110° C. and 0.1 ml, 2,5-dimethyl-2,5-di(tert-butylperoxy)-hexane (radical starter) is added. After 2 h reaction time, 1 ml 2,5-dimethyl-2,5-di(tert-butylperoxy)-hexane is again added. The viscous, light yellow reaction mixture is precipitated in 250 ml cold methanol after a reaction time of 17 h. After drying under a high vacuum, 3.80 g of a colorless, powdery product is obtained.

2.76 g of the polymer thioether and 16.16 g 3-(3,5-di-tert. butyl-4-hydroxyphenyl)propionic acid methylester are dissolved in 40 ml chloroform in a 100 m Schlenk flask. The solution is heated to 100° C. in reflux and 100 mg dibutyl tin oxide are added. The is cooled to room temperature and shaken into 300 ml cold methanol after 26 h. The precipitated product is filtered off, washed with methanol, and subsequently dried under areaction mixture high vacuum. 2.02 g of the white, powdery product are obtained. The polymer compound was confirmed by its FTIR spectrum.

IR: 3521 v(—OH), 2953 v(—CH$_2$), 1670 v(—$C_{Ester}$=O), 1155 v (para subst. aromat), 1450 v(—C—N), 931 v(=CH), 762 v(—C—S—), 697 v(=C—H mono-subst. benzyl) cm$^{-1}$.

III. APPLICATION TEST OF THE EXAMPLES IN ACCORDANCE WITH THE INVENTION a) Application test of Example A in accordance with the invention Example A in accordance with the invention was worked at the weight percentages that can be seen from Table 1 into polypropylene (Moplen HP 500N, Lyondell Basel! Industries) in comparison with a commercial phenolic antioxidant containing sulfur (Comparison example 2, Songnox 1035, Songwon). Example 1 in accordance with the invention shows the comparable weight concentration with respect to the comparison examples; Example 2 in accordance with the invention was calculated according to the mol equivalent at phenolic antioxidant groups.

TABLE 1

Compositions of the examples in accordance with the invention and comparison examples

| | |
|---|---|
| Comparison example 1 | Without additive |
| Comparison example 2 | 0.3% Songnox 1035 |

TABLE 1-continued

Compositions of the examples in accordance with
the invention and comparison examples

| | |
|---|---|
| Comparison example 3 DSTDP | 0.1% Irganox 1010/0.2% |
| Comparison example 4 DLTDP | 0.1% Irganox 1076/0.2% |
| Example 1 in accordance with the invention | 0.3% Example A |
| Example 2 in accordance with the invention | 0.39% Example A |

The following structure is understood by Songnox 1035: 2,2'-thiodiethylene bis[3-(3,5-di-tert-butyl-4-hydroxyphenyl)propionate]

DSTDP: Distearylthiodipropionate
DLDTP: Dilauryldithiopropionate

The extrusion of the compound mixtures took place in a twin screw extruder of the type Process 11 (Fisher Scientific) under the temperature profile shown in Table 2. The polymer melt is discharged at 200 r.p.m. and is cooled in a water bath and is subsequently pelletized.

TABLE 2

Temperature profile of the extrusion trials

| Zone 1 | 170° C. |
|---|---|
| Zone 2 | 180° C. |
| Zone 3 | 190° C. |
| Zone 4 | 200° C. |
| Zone 5 | 200° C. |
| Zone 6 | 200° C. |
| Zone 7 | 200° C. |

The pellets were aged in accordance with DIN EN ISO 4577.1999 in a convection furnace at 150° C. and 50% air circulation for 80 days and samples were taken after 5, 10 and 50 days. The assessment of the residual stability subsequently took place by a static OIT (oxidative induction time) measurement in accordance with DIN EN ISO 11357-6:2013 at 230° C. or 230° C. using synthetic air as the purging gas. Table 3 comprises the determined induction times. The residual stability of the polymers is the higher here, the longer the induction time is.

TABLE 3

OIT values after aging at 150° C.

| | OIT [min] after aging of | | | |
|---|---|---|---|---|
| | 230° C. | | 210° C. | |
| | 0 days | 5 days | 10 days | 50 days |
| Comparison example 1 | 3 | 0 | 0 | 0 |
| Comparison example 2 | 45 | 21 | 17 | 37 |
| Comparison example 3 | 22 | 11 | 9 | 51 |
| Comparison example 4 | 9 | # | 6 | 17 |
| Example 1 in accordance with the invention | 62 | 28 | 17 | 82 |
| Example 2 in accordance with the invention | 88 | 37 | 25 | 119 |

In the unstabilized polypropylene (Comparison example 1), the start of oxidation takes place in a very short time; there is no residual stability at all after aging. The compounds with admixed antioxidants delayed the start of oxidation. The examples in accordance with the invention surprisingly show a superior stability of the stabilizer in accordance with the invention with respect to the comparison examples.

Measurements of the yellowness index (spectro-guide sphere gloss with white standard, BYK Additives and Instruments) of the aged and unaged samples showed a much smaller discoloration tendency of the examples in accordance with the invention during the course of aging in accordance with Table 4 in contrast with the comparison examples.

TABLE 4

Yellowness index after aging at 150° C.

| | Increase in the yellowness index after aging of | | |
|---|---|---|---|
| | 5 days | 10 days | 80 days |
| Comparison example 1 | 11.6 | 86.4 | Degradation |
| Comparison example 2 | 8.6 | 16.2 | 82.91 |
| Example 1 in accordance with the invention | 1.3 | 8.7 | 33.57 |
| Example 2 in accordance with the invention | 2.2 | 11.6 | 42.05 | b) Application test of Example C in accordance with the invention

The melt volume flow rate of the aged pellets was determined in accordance with DIN EN ISO 1133-2:2011 (2.16 kg, 230° C.).

TABLE 5

Compositions of the examples in accordance with
the invention and comparison examples

| | |
|---|---|
| Comparison example 1 | Without additive |
| Comparison example 2 | 0.3% Songnox 1035 |
| Comparison example 4 | 0.1% Irganox 1076/ 0.2% DLTDP |
| Example 3 in accordance with the invention | 0.3% Example C |

Table 6 comprises the melt volume flow rates determined. The residual stability of the polymers is the higher here, the lower the melt volume flow rate is.

TABLE 6

Melt volume flow rate after aging at 150° C.

| | MVR [cm³/10 min] after aging of | | | |
|---|---|---|---|---|
| | 30 days | 60 days | 70 days | 80 days |
| Comparison example 1 | Not measurable | Not measurable | Not measurable | Not measurable |
| Comparison example 2 | 18.7 | 25.4 | Not measurable | Not measurable |
| Comparison example 4 | 19.4 | 20.9 | 22.7 | Not measurable |
| Example 3 in accordance with the invention | 17.9 | 19.4 | 21.3 | 22.7 |

In the unstabilized polypropylene (Comparison example 1), the chain degradation of the polypropylene takes place in a very short time; there is no residual stability at all after aging. The measured MVR values are thereby no longer measurable since a high degradation and thus very high MVR values (>500) are reached. The compounds with admixed antioxidants delayed the start of the chain degradation. The example in accordance with the invention surprisingly shows a superior stability of the stabilizer in accordance with the invention in the course of aging with respect to the comparison examples.

c) Application test of the examples in accordance with the invention in polypropylene filled with talcum Analog to the application test of Example A in accordance with the invention, the evaluation of the stability took place by an OIT measurement for the examples in accordance with the invention and comparison examples in Table 7 with the addition of talcum as filler at 230° C. without aging. The percentage content of admixed stabilizer here relates to the content of polypropylene.

TABLE 7

Compositions of the examples in accordance with the invention and comparison examples in polypropylene filled with Finntalc M15 (all figures in wt. %).

| Comparison example 5 | Without additive | 20% Finntalc M15 |
|---|---|---|
| Comparison example 6 | 0.1% Irganox 1076/ 0.2 % DLTDP | 20% Finntalc M15 |
| Example 4 in accordance with the invention | 0.3% Example A | 20% Finntalc M15 |
| Example 5 in accordance with the invention | 0.3% Example C | 20% Finntalc M15 |
| Example 6 in accordance with the invention | 0.3% Example F | 20% Finntalc M15 |
| Example 7 in accordance with the invention | 0.3% Example G | 20% Finntalc M15 |

TABLE 8

OIT values in PP with 20 wt. % Finntalc M15 prior to aging t 230° C.

| | OIT [min] 230° C. |
|---|---|
| Comparison example 5 | 0 |
| Comparison example 6 | 11 |
| Example 4 in accordance with the invention | 47 |
| Example 5 in accordance with the invention | 14 |
| Example 6 in accordance with the invention | 17 |
| Example 7 in accordance with the invention | 29 |

In the unstabilized polypropylene (Comparison example 5) with the Finntalc M15 filler, the start of oxidation already took place directly after the switchover from inert atmosphere to an atmosphere containing oxygen so that there is no longer any residual stability at all. The examples in accordance with the invention surprisingly show a much superior stability of the stabilizer in accordance with the invention with respect to the comparison examples.

The stabilizers in accordance with the invention were analogously worked into 10% talcum of the type Luzenac 1445 in accordance with Table 9 and the OIT was determined (Table 10).

TABLE 9

Compositions of the examples in accordance with the invention and comparison examples in polypropylene filled with Luzenac 1445 (all figures in wt. %).

| Comparison example 7 | Without additive | 10% Luzenac 1445 |
|---|---|---|
| Comparison example 8 | 0.1% Irganox 107/ 0.2% DLTDP | 10% Luzenac 1445 |

TABLE 9-continued

Compositions of the examples in accordance with the invention and comparison examples in polypropylene filled with Luzenac 1445 (all figures in wt. %).

| Example 8 in accordance with the invention | 0.3% Example A | 10% Luzenac 1445 |
|---|---|---|
| Example 9 in accordance with the invention | 0.2% Example A | 10% Luzenac 1445 |
| Example 10 in accordance with the invention | 0.3% Example B | 10% Luzenac 1445 |
| Example 11 in accordance with the invention | 0.3% Example C | 10% Luzenac 1445 |
| Example 12 in accordance with the invention | 0.1% Example C | 10% Luzenac 1445 |
| Example 13 in accordance with the invention | 0.3% Example F | 10% Luzenac 1445 |
| Example 14 in accordance with the invention | 0.1% Example F | 10% Luzenac 1445 |
| Example 15 in accordance with the invention | 0.3% Example G | 10% Luzenac 1445 |
| Example 16 in accordance with the invention | 0.3% Example I | 10% Luzenac 1445 |

TABLE 10

OIT values in PP with 10 wt. % Luzenac 1445 prior to aging.

| | OIT [min] prior to aging 230° C. |
|---|---|
| Comparison example 7 | 5 |
| Comparison example 8 | 8 |
| Example 8 in accordance with the invention | 85 |
| Example 9 in accordance with the invention | 62 |
| Example 10 in accordance with the invention | 60 |
| Example 11 in accordance with the invention | 35 |
| Example 12 in accordance with the invention | 12 |
| Example 13 in accordance with the invention | 46 |
| Example 14 in accordance with the invention | 12 |
| Example 15 in accordance with the invention | 43 |
| Example 16 in accordance with the invention | 41 |

In the unstabilized polypropylene (Comparison example 7) with the Luzenac 1445 filler, the start of oxidation already takes place at a very early time. The examples in accordance with the invention show a much superior stability of the stabilizers in accordance with the invention with respect to the comparison examples even at comparatively lower concentrations (examples in accordance with the invention 9, 12, and 14).

d) Application test of the examples in accordance with the invention in further systems Compound A in accordance with the invention was furthermore worked into the following polymers in a concentration of 0.3%.

D1: Acrylonitrile butadiene styrene (ABS)

D2: Polyamide-6

D3: Polyamide-6 with 30% glass fibers

D4: Polybutylene terephthalate

In all cases, an improved long-term stability, i.e. maintaining of the mechanical properties, can be demonstrated with respect to the polymers without additive.

The invention claimed is:

1. A compound selected from the group consisting of

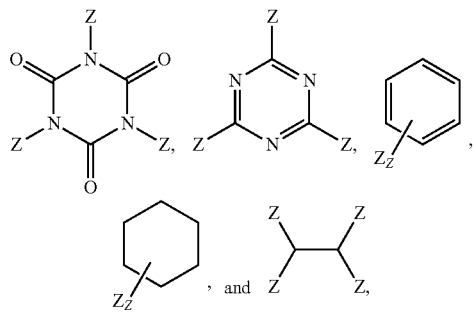

wherein Z is

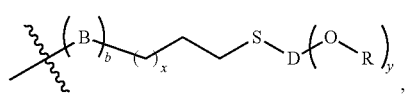

and wherein the variables B, D, R, b, x, y, and z each has the following definition independently of one another:

B O or NH;
D a linear or branched aliphatic residue having 1 to 12 carbon atoms;
R a residue having at least one sterically hindered hydroxyphenyl residue;
b 0 or 1;
x 0 to 12;
y 1 to 4; and
z 2, 3, or 4, wherein the at least one sterically hindered hydroxyphenyl residue has the formula:

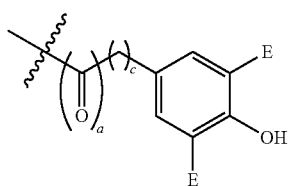

wherein

E is the same or different on every occurrence and represents a linear aliphatic, branched aliphatic, or cycloaliphatic alkyl residue having 1 to 18 carbon atoms, an aromatic residue having 6 to 36 carbon atoms, or hydrogen;
a is 1 or 0; and
c is 0, 1, 2, 3, or 4.

2. The compound of claim 1, wherein variables x and y have the following meaning respectively independently of one another:

x 0 or 1;
y 1 or 2.

3. The compound of claim 1, wherein D is —CH$_2$—.

4. The compound of claim 1, which is selected from the group consisting of the following compounds:

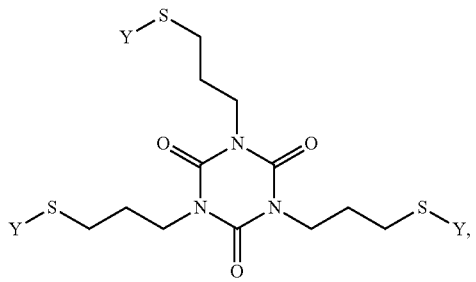

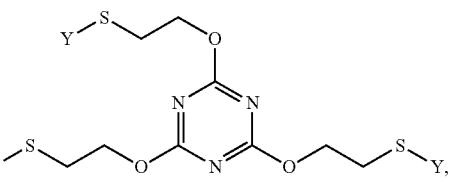

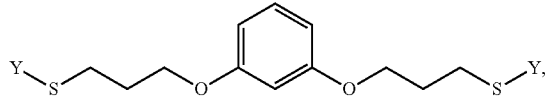

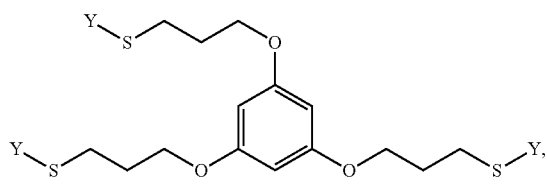

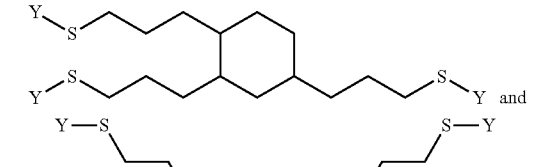

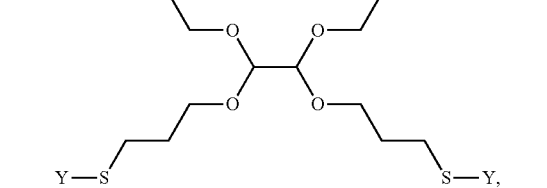

wherein the residue Y has the following meaning on every occurrence:

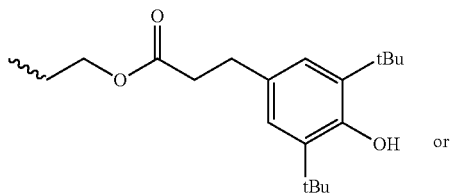

-continued

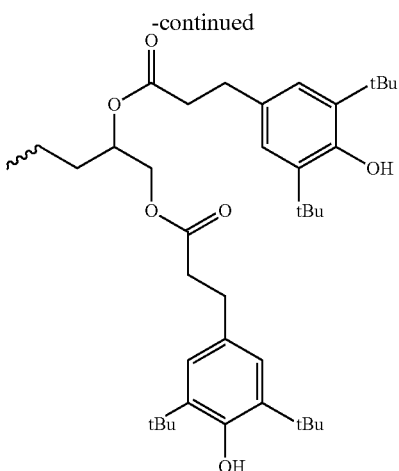

wherein in the above residues, the tBu residue can also be substituted in full or in part by a methyl group.

5. A method of preparing a compound of claim 1, wherein a compound selected from the group consisting of the following compounds

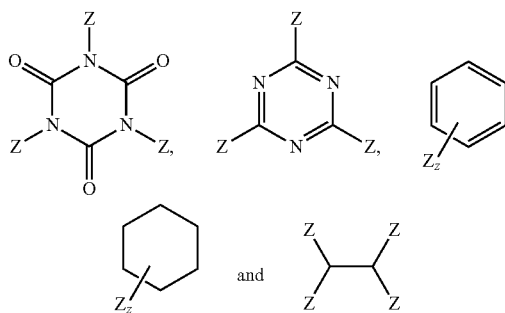

wherein Z is:

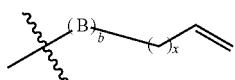

wherein the variables B, b, x each has the following definition independently of one another:
B O or NH;
b 0 or 1;
x 0 to 12; and
z 2 3 or 4;
is reacted with a thiol of the following formula:

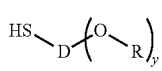

wherein the variables D, R, y each has the following definition independently of one another:
D a linear or branched aliphatic residue having 1 to 12 carbon atoms;
R a residue having at least one sterically hindered hydroxyphenyl residue; and
y 1 to 4; and
wherein the at least one sterically hindered hydroxyphenyl residue has the formula:

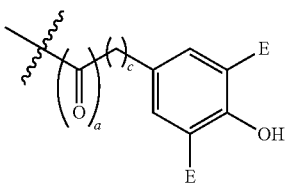

wherein
E is the same or different on every occurrence and represents a linearly aliphatic, branched aliphatic, or cycloaliphatic alkyl residue having 1 to 18 carbon atoms or an aromatic residue having 6 to 36 carbon atom or hydrogen;
a is 1 or 0; and
c is 0, 1, 2, 3, or 4.

6. The method of claim 5, wherein the reaction of the compound with the thiol is carried out with an excess of the thiol with respect to the unsaturated function of the compound.

7. A composition comprising at least one organic component to be stabilized and at least one compound in accordance with claim 1.

8. The composition of claim 7, wherein the component to be stabilized is selected from the group consisting of plastics, oils, lubricants, and fats.

9. The composition of claim 7, which comprises:
95.00 to 99.99 wt% of at least one component to be stabilized and
0.01 to 5.00 wt% of the at least one compound.

10. The composition of claim 7, which additionally includes at least one additive selected from the group consisting of UV absorbers, light stabilizers, stabilizers, antioxidants, hydroxyl amines, benzofurans, metal deactivators, filler deactivators, antiozonants, nucleation agents, impact strength improvers, plasticizers, lubricants, rheology modifiers, thixotropic agents, chain extenders, processing aids, demolding aids, flame retardants, pigments, dyes, optical brighteners, antimicrobial agents, antistatic agents, slip agents, antiblocking agents, coupling agents, crosslinking agents, anti-crosslinking agents, hydrophilization agents, hydrophobization agents, bonding agents, dispersion agents, degradation additives, defoaming aids, odor traps, marking agents, antifogging agents, fillers, and reinforcements.

11. The composition of claim 7, which additionally includes at least one additive selected from the group consisting of phosphites, phosphonites, hydroxylamines, and nitrons.

12. A method of stabilizing an organic component to be stabilized, the method comprising mixing with, or working into, at least one compound of claim 1 with the organic component to be stabilized.

13. The method of claim 12, wherein the organic component is stabilized with respect to oxidative, thermal, or actinic degradation or damage.

* * * * *